(12) United States Patent
Kimura et al.

(10) Patent No.: US 8,790,855 B2
(45) Date of Patent: Jul. 29, 2014

(54) CHARGE CONTROL AGENT AND TONER USING SAME

(75) Inventors: Ikuo Kimura, Tsukuba (JP); Motonori Tsuji, Tsukuba (JP); Masami Ito, Tsukuba (JP); Masaya Tojo, Tsukuba (JP); Kanae Hiraishi, Tsukuba (JP)

(73) Assignee: Hodogaya Chemical Co., Ltd, Tokyo (JP)

( * ) Notice: Subject to any disclaimer, the term of this patent is extended or adjusted under 35 U.S.C. 154(b) by 0 days.

(21) Appl. No.: 13/821,755

(22) PCT Filed: Sep. 1, 2011

(86) PCT No.: PCT/JP2011/069947
§ 371 (c)(1),
(2), (4) Date: Mar. 8, 2013

(87) PCT Pub. No.: WO2012/035990
PCT Pub. Date: Mar. 22, 2012

(65) Prior Publication Data
US 2013/0177843 A1    Jul. 11, 2013

(30) Foreign Application Priority Data
Sep. 13, 2010   (JP) .................. 2010-203972

(51) Int. Cl.
*G03G 9/097*   (2006.01)

(52) U.S. Cl.
USPC ............. 430/108.21; 430/108.2; 548/183; 546/269.7; 546/270.4; 544/336; 544/216

(58) Field of Classification Search
USPC ........ 430/108.2, 108.21; 548/183; 546/269.7, 546/270.4; 544/336, 216
See application file for complete search history.

(56) References Cited

U.S. PATENT DOCUMENTS

| | | | |
|---|---|---|---|
| 4,206,064 A | 6/1980 | Kiuchi et al. | |
| 4,338,390 A | 7/1982 | Lu | |

(Continued)

FOREIGN PATENT DOCUMENTS

| | | |
|---|---|---|
| JP | 55-42752 B2 | 11/1980 |
| JP | 57-111541 A | 7/1982 |

(Continued)

OTHER PUBLICATIONS

Nori Matsui et al., "An Analysis of the Charging Properties of Model Toner Containing Carbon Black", Electrophotography—The Society Journal, 1988, pp. 307-311, vol. 27, No. 2.

(Continued)

*Primary Examiner* — Peter Vajda
(74) *Attorney, Agent, or Firm* — Sughrue Mion, PLLC

(57) ABSTRACT

The present invention provides a charge control agent containing, as an active substance(s), one or two or more thiazolidinedione derivatives represented by the following formula (1),

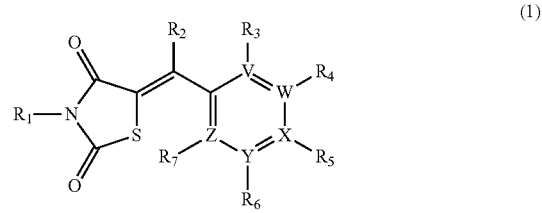

(1)

where $R_1$ represents a hydrogen atom, etc.; $R_2$ represents a hydrogen atom, a linear or branched alkyl group having 1 to 8 carbon atoms which may have a substituent, etc.; $R_3$ to $R_7$, which may be identical to or different from each other, represent a hydrogen atom, a chlorine atom, a linear or branched alkyl group having 1 to 8 carbon atoms which may have a substituent, etc., and may be joined to each other to form a ring; and V, W, X, Y and Z represent a carbon atom or a nitrogen atom, and 0 to 3 of any of V, W, X, Y and Z are nitrogen atoms which do not have the substituents of $R_3$ to $R_7$.

12 Claims, 2 Drawing Sheets

(56) References Cited

U.S. PATENT DOCUMENTS

| | | | |
|---|---|---|---|
| 4,356,244 A * | 10/1982 | Leichter et al. ............... 430/82 |
| 4,391,890 A | 7/1983 | Lu | |
| 4,394,430 A | 7/1983 | Jadwin et al. | |
| 4,396,697 A | 8/1983 | Ciccarelli et al. | |
| 4,767,688 A | 8/1988 | Hashimoto et al. | |
| 2009/0208863 A1 | 8/2009 | Kouyama et al. | |

FOREIGN PATENT DOCUMENTS

| | | |
|---|---|---|
| JP | 57-119364 A | 7/1982 |
| JP | 58-9154 A | 1/1983 |
| JP | 58-98742 A | 6/1983 |
| JP | 61-3149 A | 1/1986 |
| JP | 61-69073 A | 4/1986 |
| JP | 61-141453 A | 6/1986 |
| JP | 61-221756 A | 10/1986 |
| JP | 62-94856 A | 5/1987 |
| JP | 1-306861 A | 12/1989 |
| JP | 2568675 B2 | 1/1997 |
| JP | 2899038 B2 | 6/1999 |
| JP | 3313871 B2 | 8/2002 |
| JP | 3325730 B2 | 9/2002 |
| JP | 3359657 B2 | 12/2002 |
| JP | 2003-162100 A | 6/2003 |
| JP | 2003-295522 A | 10/2003 |
| JP | 2009-192984 A | 8/2009 |
| JP | 2010-111750 A | 5/2010 |
| WO | 2007/111346 A1 | 4/2007 |
| WO | 2007/119797 A1 | 10/2007 |

OTHER PUBLICATIONS

International Search Report for PCT/JP2011/069947 dated Dec. 6, 2011.
English translation of the International Preliminary Report on Patentability and Written Opinion mailed Apr. 18, 2013 for counterpart International Application No. PCT/JP2011/069947.

* cited by examiner

CHARGE CONTROL AGENT AND TONER USING SAME

CROSS REFERENCE TO RELATED APPLICATIONS

This application is a National Stage of International Application No. PCT/JP2011/069947 filed Sep. 1, 2011, claiming priority based on Japanese Patent Application No. 2010-203972 filed Sep. 13, 2010, the contents of all of which are incorporated herein by reference in their entirety.

TECHNICAL FIELD

The present invention relates to a charge control agent for use in an image-forming apparatus for developing an electrostatic latent image in the fields of electrophotography, electrostatic recording etc., and a negatively charged toner containing the charge control agent.

BACKGROUND ART

In an image-forming process of an electrophotographic system, an electrostatic latent image is formed on an inorganic photoreceptor formed of selenium, a selenium alloy, cadmium sulfate, amorphous silicon, etc. or an organic photoreceptor using a charge generation materials and a charge transport materials, developed with a toner, and transferred and fixed to a paper sheet or a plastic film to obtain a visible image.

Photoreceptors are classified into positively charged ones and negatively charged ones depending upon their structures. In the case where a printed portion is allowed to remain as an electrostatic latent image by light exposure, the latent image is developed with a toner charged with reverse polarity. In contrast, in the case where a printed portion is electrically discharged and subjected to reversal development, the printed portion is developed with a toner charged with the same polarity.

A toner contains a binder resin, a colorant and other additives. To impart desirable charging characteristics (charge rate, charge level, charge stability, etc.), temporal stability, environmental stability and the like, a charge control agent is generally added. Owing to the addition of the charge control agent, the characteristics of a toner are greatly improved.

Examples of a positive triboelectric charge control agent presently known in the art include a nigrosine dye, an azine dye, a copper phthalocyanine pigment, a quaternary ammonium salt and a polymer having a quaternary ammonium salt at a side chain. Examples of a negative triboelectric charge control agent presently known in the art include metal complexes of a monoazo dye, metal complexes of salicylic acid, naphthoic acid and dicarboxylic acid, a copper phthalocyanine pigment and a resin containing an acid component.

Furthermore, in the case of a color toner, market expansion of which is expected in the future, a pale-colored charge control agent having little effect on hue, desirably a colorless charge control agent, is indispensable. Examples of such a pale-colored or colorless charge control agent for use in a negatively charged toner include metal complex compounds of hydroxy benzoate derivatives (see, for example, Patent Literatures 1 to 3), metal salt compounds of aromatic dicarboxylic acids (see, for example, Patent Literature 4), metal complex compounds of anthranilic acid derivatives (see, for example, Patent Literatures 5 and 6), organic boron compounds (see, for example, Patent Literatures 7 and 8), biphenol compounds (see, for example, Patent Literature 9), calix[n]arene compounds (see, for example, Patent Literatures 10 to 15) and cyclic phenol sulfates (see, for example, Patent Literatures 16 to 18). Furthermore, examples thereof for use in a positively charged toner include quaternary ammonium salt compounds (see, for example, Patent Literatures 19 to 21).

CITATION LIST

Patent Literatures

Patent Literature 1: Japanese Examined Patent Publication No. 55-042752
Patent Literature 2: Japanese Patent Application Laid-Open No. 61-069073
Patent Literature 3: Japanese Patent Application Laid-Open No. 61-221756
Patent Literature 4: Japanese Patent Application Laid-Open No. 57-111541
Patent Literature 5: Japanese Patent Application Laid-Open No. 61-141453
Patent Literature 6: Japanese Patent Application Laid-Open No. 62-094856
Patent Literature 7: U.S. Pat. No. 4,767,688
Patent Literature 8: Japanese Patent Application Laid-Open No. 01-306861
Patent Literature 9: Japanese Patent Application Laid-Open No. 61-003149
Patent Literature 10: Japanese Patent No. 2568675
Patent Literature 11: Japanese Patent No. 2899038
Patent Literature 12: Japanese Patent No. 3359657
Patent Literature 13: Japanese Patent No. 3313871
Patent Literature 14: Japanese Patent No. 3325730
Patent Literature 15: Japanese Patent Application Laid-Open No. 2003-162100
Patent Literature 16: Japanese Patent Application Laid-Open No. 2003-295522
Patent Literature 17: WO2007-111346
Patent Literature 18: WO2007-119797
Patent Literature 19: Japanese Patent Application Laid-Open No. 57-119364
Patent Literature 20: Japanese Patent Application Laid-Open No. 58-009154
Patent Literature 21: Japanese Patent Application Laid-Open No. 58-098742

Non Patent Literatures

Non Patent Literature 1: ELECTROPHOTOGRAPHY—The Society Journal—, Vol. 27, No. 2, p307 to 311 (1988)

SUMMARY OF INVENTION

Problems to be Solved by the Invention

However, most of these charge control agents are complexes formed of heavy metals such as chromium or salts thereof. They have a problem in view of waste regulation and are not always safe. Furthermore, a completely colorless product cannot be obtained from them. The charge-imparting effect is low compared to that presently demanded. Since the rising rate of charging is insufficient, copy images obtained in the beginning are lack of sharpness. When copies are made in a continuously operation, the quality of copy images tends to vary. Furthermore, they cannot be applied to a polymerized toner. Likewise, they have these drawbacks. Thus, it has been desired to develop a charge control agent having a high charge-imparting effect and applicable to a polymerized toner.

The present invention was made to solve the aforementioned problems and is directed to providing a charge control agent having a sharp charge rising rate and a high charge amount, and in addition having safeness without any problem in waste regulation. Furthermore, the present invention is directed to providing a negatively charged toner containing the charge control agent and having high charging performance, for developing an electrostatic latent image.

Means for Solving the Problems

Intensive studies have been conducted with the view to attaining the aforementioned objects. As a result, the present invention was attained. The gist of the invention is as follows.

The present invention provides a charge control agent containing, as an active substance(s), one or two or more thiazolidinedione derivatives represented by formula (1).

[Chemical Formula 1]

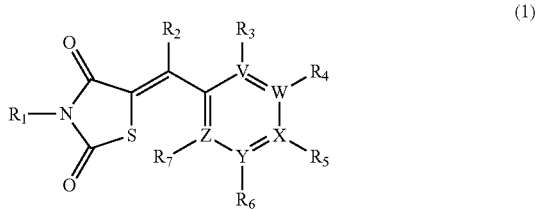

(1)

In formula (1), $R_1$ represents a hydrogen atom, a linear or branched alkyl group having 1 to 8 carbon atoms which may have a substituent, a cycloalkyl group having 5 to 10 carbon atoms which may have a substituent, a substituted or unsubstituted aromatic hydrocarbon group, a substituted or unsubstituted heterocyclic group or a substituted or unsubstituted condensed polycyclic aromatic group; $R_2$ represents a hydrogen atom, a linear or branched alkyl group having 1 to 8 carbon atoms which may have a substituent, a cycloalkyl group having 5 to 10 carbon atoms which may have a substituent, a linear or branched alkenyl group having 2 to 6 carbon atoms which may have a substituent, a linear or branched alkyloxy group having 1 to 8 carbon atoms which may have a substituent, a cycloalkyloxy group having 5 to 10 carbon atoms which may have a substituent, a substituted or unsubstituted aromatic hydrocarbon group, a substituted or unsubstituted heterocyclic group, a substituted or unsubstituted condensed polycyclic aromatic group or a substituted or unsubstituted aryloxy group; $R_3$ to $R_7$, which may be identical to or different from each other, represent a hydrogen atom, a deuterium atom, a fluorine atom, a chlorine atom, a bromine atom, an iodine atom, a hydroxy group, a cyano group, a trifluoromethyl group, a nitro group, a linear or branched alkyl group having 1 to 10 carbon atoms which may have a substituent, a cycloalkyl group having 5 to 10 carbon atoms which may have a substituent, a linear or branched alkenyl group having 2 to 6 carbon atoms which may have a substituent, a linear or branched alkyloxy group having 1 to 8 carbon atoms which may have a substituent, a cycloalkyloxy group having 5 to 10 carbon atoms which may have a substituent, a substituted or unsubstituted aromatic hydrocarbon group, a substituted or unsubstituted heterocyclic group, a substituted or unsubstituted condensed polycyclic aromatic group or a substituted or unsubstituted aryloxy group, and may be mutually joined to form a ring; and V, W, X, Y and Z represent a carbon atom or a nitrogen atom and 0 to 3 of any of V, W, X, Y and Z are a nitrogen atom which does not have substituents of $R_3$ to $R_7$.

The present invention also provides a toner containing, as an active substance(s), one or two or more thiazolidinedione derivatives represented by the formula (1), a colorant and a binder resin.

The present invention also provides a polymerized toner containing, as an active substance(s), one or two or more thiazolidinedione derivatives represented by the formula (1), a colorant and a binder resin.

A charge control agent containing, as an active substance(s), one or two or more thiazolidinedione derivatives represented by the above formula (1) has excellent properties such as a fast charge rising rate and a high charge amount as well as no problem in waste regulation and safeness, and thus, the charge control agent can be suitably used for controlling charge of toner. Accordingly, it can be said that the present invention is directed to use of a charge control agent containing, as an active substance(s), one or two or more of the thiazolidinedione derivatives represented by the above formula (1) for controlling charge of toner or directed to application of a charge control agent containing, as an active substance(s), one or two or more thiazolidinedione derivatives represented by the above formula (1) to controlling charge of toner. The above toner may be a polymer toner.

Furthermore, it can be said that the present invention is directed to a method for controlling charge of toner by using a charge control agent containing, as an active substance(s), one or two or more thiazolidinedione derivatives represented by the above formula (1). In this case, the above toner may be a polymer toner.

Effects of the Invention

In the present invention, the charge control agent containing, as an active substance(s), one or two or more thiazolidinedione derivatives represented by formula (1) has a sharp rising rate of charging than a conventional charge control agent and a high charge amount and having charging characteristics particularly excellent in temporal stability and environmental stability. Furthermore, heavy metals such as chromium, which is an environmental concern, are not contained and further, dispersibility and stability of the compound are excellent. The charge control agent is useful as an electrophotographic charge control agent which enables a toner to exhibit sufficient triboelectric property, particularly useful for use in a color toner and further in a polymerized toner.

EMBODIMENTS FOR CARRYING OUT THE INVENTION

Figure 1:
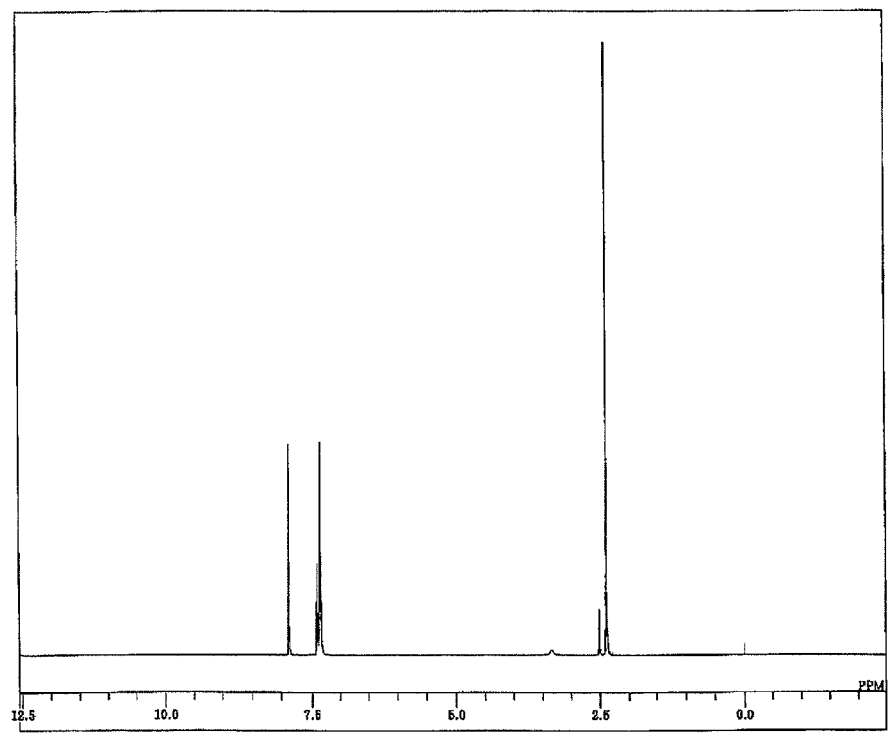
FIG. 1 is a $^1$H-NMR chart of a compound (Exemplary Compound No. 3) of Synthesis Example 2.

Embodiments for carrying out the present invention will be described in detail. Note that the present invention is not limited to the following embodiments and can be carried out by modifying it in various ways within the range of the gist of the invention.

The charge control agent according to the embodiment contains, as an active substance(s), one or two or more thiazolidinedione derivatives represented by the formula (1). First, a thiazolidinedione derivative represented by the formula (1) will be described.

In the "linear or branched alkyl group having 1 to 8 carbon atoms which may have a substituent" or "cycloalkyl group having 5 to 10 carbon atoms which may have a substituent" represented by $R_1$ in formula (1), specific examples of the "linear or branched alkyl group having 1 to 8 carbon atoms" or "cycloalkyl group having 5 to 10 carbon atoms" include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group, an isooctyl group, a cyclopentyl group, a cyclohexyl group, a 1-adamantyl group and a 2-adamantyl group.

As the "linear or branched alkyl group having 1 to 8 carbon atoms which may have a substituent" represented by $R_1$ in formula (1), a "linear or branched alkyl group having 1 to 4 carbon atoms which may have a substituent" is preferable. As the "cycloalkyl group having 5 to 10 carbon atoms which may have a substituent," a "cycloalkyl group having 5 to 6 carbon atoms which may have a substituent" is preferable.

In the "linear or branched alkyl group having 1 to 8 carbon atoms, which has a substituent" or "cycloalkyl group having 5 to 10 carbon atoms, which has a substituent" represented by $R_1$ in formula (1), specific examples of a "substituent" include a deuterium atom, a trifluoromethyl group, a cyano group, a nitro group; halogen atoms such as a fluorine atom, a chlorine atom, a bromine atom and an iodine atom; linear or branched alkyl groups having 1 to 8 carbon atoms such as a methyl group, an ethyl group, a n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; linear or branched alkoxy groups having 1 to 8 carbon atoms such as a methoxy group, an ethoxy group and a propyloxy group; alkenyl groups such as an allyl group; aralkyl groups such as a benzyl group, a naphthylmethyl group and a phenethyl group; aryloxy groups such as a phenoxy group and a tolyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group; heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic groups, such as a diphenylamino group and a dinaphthylamino group; diaralkylamino groups such as a dibenzylamino group and a diphenethylamino group; di-substituted amino groups substituted with a heterocyclic group, such as a dipyridylamino group and a dithienylamino group and a dipiperidinylamino group; dialkenylamino groups such as a diallylamino group; and di-substituted amino groups substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In the "linear or branched alkyl group having 1 to 8 carbon atoms which may have a substituent," "cycloalkyl group having 5 to 10 carbon atoms which may have a substituent" or "linear or branched alkenyl group having 2 to 6 carbon atoms which may have a substituent" represented by $R_2$ in formula (1), specific examples of the "linear or branched alkyl group having 1 to 8 carbon atoms," "cycloalkyl group having 5 to 10 carbon atoms" or "linear or branched alkenyl group having 2 to 6 carbon atoms" include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group, an isooctyl group, a cyclopentyl group, a cyclohexyl group, a 1-adamantyl group, a 2-adamantyl group, a vinyl group, an allyl group, an isopropenyl group and a 2-butenyl group. They may mutually bind via a single bond, an oxygen atom or a sulfur atom to form a ring.

As the "linear or branched alkyl group having 1 to 8 carbon atoms which may have a substituent" represented by $R_2$ in formula (1), a "linear or branched alkyl group having 1 to 6 carbon atoms which may have a substituent" is preferable and a "linear or branched alkyl group having 1 to 4 carbon atoms which may have a substituent" is more preferable.

Furthermore, as the "cycloalkyl group having 5 to 10 carbon atoms which may have a substituent" represented by $R_2$ in formula (1), a "cycloalkyl group having 5 or 6 carbon atoms which may have a substituent" is preferable.

In the "linear or branched alkyl group having 1 to 8 carbon atoms, which has a substituent," "cycloalkyl group having 5 to 10 carbon atoms, which has a substituent" or "linear or branched alkenyl group having 2 to 6 carbon atoms, which has a substituent" represented by $R_2$ in formula (1), specific examples of the "substituent" include a deuterium atom, a trifluoromethyl group, a cyano group and a nitro group; halogen atoms such as a fluorine atom, a chlorine atom, a bromine atom and an iodine atom; linear or branched alkyl groups having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; linear or branched alkoxy groups having 1 to 8 carbon atoms such as a methoxy group, an ethoxy group and a propyloxy group; alkenyl groups such as allyl group; aralkyl groups such as a benzyl group, a naphthylmethyl group and a phenethyl group; aryloxy groups such as a phenoxy group and a tolyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group; heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic group, such as a diphenylamino group and a dinaphthylamino group; diaralkylamino groups such as a dibenzylamino group and a diphenethylamino group; di-substituted amino groups substituted with a heterocyclic group, such as a dipyridylamino group, a dithienylamino group and a dipiperidinyl amino group; dialkenylamino groups such as a diallylamino group; and di-substituted amino groups substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In the "linear or branched alkyl group having 1 to 10 carbon atoms which may have a substituent", "cycloalkyl group having 5 to 10 carbon atoms which may have a substituent" or "linear or branched alkenyl group having 2 to 6 carbon atoms which may have a substituent" represented by $R_3$ to $R_7$ in formula (1), specific examples of the "linear or branched alkyl group having 1 to 8 carbon atoms," "cycloalkyl group having 5 to 10 carbon atoms" or "linear or branched alkenyl group having 2 to 6 carbon atoms" include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group, an isooctyl group, a nonyl group, a decyl group, a cyclopentyl group, a cyclohexyl group, a 1-adamantyl group, a 2-adamantyl group, a vinyl group, an allyl group, an isopropenyl group and a 2-butenyl group. They may mutually bind via a single bond, an oxygen atom or a sulfur atom to form a ring.

As the "linear or branched alkyl group having 1 to 10 carbon atoms which may have a substituent" represented by $R_3$ to $R_7$ in formula (1), a "linear or branched alkyl group having 1 to 8 carbon atoms which may have a substituent" is preferable, a "linear or branched alkyl group having 1 to 6 carbon atoms which may have a substituent" is more preferable and a "linear or branched alkyl group having 1 to 4 carbon atoms which may have a substituent" is particularly preferable.

As the "cycloalkyl group having 5 to 10 carbon atoms which may have a substituent" represented by $R_3$ to $R_7$ in formula (1), a "cycloalkyl group having 5 and 6 carbon atoms which may have a substituent" is preferable. As the "linear or branched alkenyl group having 2 to 6 carbon atoms which may have a substituent," the "alkenyl group having 2 to 4 carbon atoms which may have a substituent" is preferable.

In the "linear or branched alkyl group having 1 to 10 carbon atoms, which has a substituent", "cycloalkyl group having 5 to 10 carbon atoms, which has a substituent" or "linear or branched alkenyl group having 2 to 6 carbon atoms, which has a substituent" represented by $R_3$ to $R_7$ in formula (1), specific examples of the "substituent" include a deuterium atom, a trifluoromethyl group, a cyano group and a nitro group; halogen atoms such as a fluorine atom, a chlorine atom, a bromine atom and an iodine atom; linear or branched alkyl groups having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; linear or branched alkoxy groups having 1 to 8 carbon atoms such as a methoxy group, an ethoxy group and a propyloxy group; alkenyl groups such as an allyl group; aralkyl groups such as a benzyl group, a naphthylmethyl group and a phenethyl group; aryloxy groups such as a phenoxy group and a tolyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group; heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic group, such as a diphenylamino group and a dinaphthylamino group; diaralkylamino groups such as a dibenzylamino group and a diphenethylamino group; di-substituted amino groups substituted with a heterocyclic group, such as a dipyridylamino group, a dithienylamino group and a dipiperidinyl amino group; dialkenylamino groups such as a diallylamino group; and di-substituted amino group substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In the "linear or branched alkyloxy group having 1 to 8 carbon atoms which may have a substituent" or "cycloalkyloxy group having 5 to 10 carbon atoms which may have a substituent" represented by $R_2$ to $R_7$ in formula (1), specific examples of the "linear or branched alkyloxy group having 1 to 8 carbon atoms" or "cycloalkyloxy group having 5 to 10 carbon atoms" include a methyloxy group, an ethyloxy group, an n-propyloxy group, an isopropyloxy group, an n-butyloxy group, a tert-butyloxy group, an n-pentyloxy group, an n-hexyloxy group, an n-heptyloxy group, an isoheptyloxy group, an n-octyloxy group, an isooctyloxy group, a cyclopentyloxy group, a cyclohexyloxy group, a cycloheptyloxy group, a cyclooctyloxy group, a 1-adamantyloxy group and 2-adamantyloxy group. They may mutually bind via a single bond, an oxygen atom or a sulfur atom to form a ring.

As the "linear or branched alkyloxy group having 1 to 8 carbon atoms which may have a substituent" represented by $R_2$ in formula (1), a "linear or branched alkyloxy group having 1 to 4 carbon atoms which may have a substituent" is preferable. As the "cycloalkyloxy group having 5 to 10 carbon atoms which may have a substituent," a "cycloalkyloxy group having 5 to 6 carbon atoms which may have a substituent" is preferable.

As the "linear or branched alkyloxy group having 1 to 8 carbon atoms which may have a substituent" represented by $R_3$ to $R_7$ in formula (1), a "linear or branched alkyloxy group having 1 to 6 carbon atoms which may have a substituent" is preferable, and a "linear or branched alkyloxy group having 1 to 4 carbon atoms which may have a substituent" is more preferable.

Furthermore, as the "cycloalkyloxy group having 5 to 10 carbon atoms which may have a substituent" represented by $R_3$ to $R_7$ in formula (1), a "cycloalkyloxy group having 5 or 6 carbon atoms which may have a substituent" is preferable.

In the "linear or branched alkyloxy group having 1 to 8 carbon atoms, which has a substituent" or "cycloalkyloxy group having 5 to 10 carbon atoms, which has a substituent" represented by $R_2$ to $R_7$ in formula (1), specific examples of the "substituent" include a deuterium atom, a trifluoromethyl group, a cyano group, a nitro group; halogen atoms such as a fluorine atom, a chlorine atom, a bromine atom and an iodine atom; linear or branched alkyl groups having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; linear or branched alkoxy groups having 1 to 8 carbon atoms such as a methoxy group, an ethoxy group and a propyloxy group; an alkenyl group such as an allyl group; aralkyl groups such as a benzyl group, a naphthylmethyl group and a phenethyl group; aryloxy groups such as a phenoxy group and a tolyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group; heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic group, such as a diphenylamino group and a dinaphthylamino group; diaralkylamino groups such as a dibenzylamino group and a diphenethylamino group; di-substituted amino group substituted with a heterocyclic group, such as a dipyridylamino group, a dithienylamino group and a dipiperidinyl amino group; dialkenylamino groups such as a diallylamino group; and di-substituted amino groups substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In the "substituted or unsubstituted aromatic hydrocarbon group," "substituted or unsubstituted heterocyclic group" or "substituted or unsubstituted condensed polycyclic aromatic group" represented by $R_1$ to $R_7$ in formula (1), specific examples of the "aromatic hydrocarbon group," "heterocyclic group" or "condensed polycyclic aromatic group" include a phenyl group, a biphenylyl group, a terphenylyl group, a naphthyl group, an anthryl group, a phenanthryl group, a fluorenyl group, an indenyl group, a pyrenyl group, a perylenyl group, a fluoranthenyl group, a triphenylenyl group, a pyridyl group, a furanyl group, a pyranyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group. They may mutually bind via a single bond, an oxygen atom or a sulfur atom to form a ring.

In the "substituted aromatic hydrocarbon group," "substituted heterocyclic group" or "substituted condensed polycyclic aromatic group" represented by $R_1$ to $R_7$ in formula (1), specific examples of the "substituent" include a deuterium atom, a cyano group, a trifluoromethyl group, a nitro group; halogen atoms such as a fluorine atom, a chlorine atom, a bromine atom and an iodine atom; linear or branched alkyl groups having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; cycloalkyl groups having 5 to 10 carbon atoms such as a cyclopentyl group and a cyclohexyl group; linear or branched alkenyl groups having 2 to 6 carbon atoms such as a vinyl group, an allyl group, a 2-butenyl group and a 1-hexenyl group; linear or branched alkyloxy groups having 1 to 8 carbon atoms such as a methoxy group, an ethoxy group and a propyloxy group; cycloalkyloxy groups having 5 to 10 carbon atoms such as a cyclopentyloxy group and a cyclohexyloxy group; aralkyl groups such as a benzyl group, a naphthylmethyl group and a phenethyl group; aryloxy groups such as a phenoxy group, a tolyloxy group, a biphenylyloxy group, a terphenylyloxy group, a naphthyloxy group, an anthryloxy group, a phenanthryloxy group, a fluorenyloxy group, an indenyloxy group, a pyrenyloxy group and a perylenyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group;

heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic group, such as a diphenylamino group and a dinaphthylamino group; diaralkylamino groups such as a dibenzylamino group and a diphenethylamino group; di-substituted amino groups substituted with a heterocyclic group, such as a dipyridylamino group, a dithienylamino group and a dipiperidinyl amino group; dialkenylamino groups such as a diallylamino group; and di-substituted amino groups substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In the "substituted or unsubstituted aryloxy group" represented by $R_2$ to $R_7$ in formula (1), specific examples of the "aryloxy group" include a phenoxy group, a tolyloxy group, a biphenylyloxy group, a terphenylyloxy group, a naphthyloxy group, an anthryloxy group, a phenanthryloxy group, a fluorenyloxy group, an indenyloxy group, a pyrenyloxy group and a perylenyloxy group. They may mutually bind via a single bond, an oxygen atom or a sulfur atom to form a ring.

In the "substituted aryloxy group" represented by $R_2$ to $R_7$ in formula (1), specific examples of the "substituent" include a deuterium atom, a cyano group, a trifluoromethyl group and a nitro group; halogen atoms such as a fluorine atom, a chlorine atom, a bromine atom and an iodine atom; linear or branched alkyl groups having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; cycloalkyl groups having 5 to 10 carbon atoms such as a cyclopentyl group and a cyclohexyl group; linear or branched alkenyl groups having 2 to 6 carbon atoms such as a vinyl group, an allyl group, a 2-butenyl group and a 1-hexenyl group; linear or branched alkyloxy groups having 1 to 8 carbon atoms such as a methoxy group, an ethoxy group and a propyloxy group; cycloalkyloxy groups having 5 to 10 carbon atoms such as a cyclopentyloxy group and a cyclohexyloxy group; aralkyl groups such as a benzyl group, a naphthylmethyl group and a phenethyl group; aryloxy groups such as a phenoxy group, a tolyloxy group, a biphenylyloxy group, a terphenylyloxy group, a naphthyloxy group, an anthryloxy group, a phenanthryloxy group, a fluorenyloxy group, an indenyloxy group, a pyrenyloxy group and a perylenyloxy group; arylalkoxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group and a triphenylenyl group; heterocyclic groups such as a pyridyl group, a furanyl group, a pyranyl group, a thienyl group, a furyl group, a pyrrolyl group, a thiophenyl group, a pyrrolidinyl group, an imidazolyl group, an imidazolinyl group, an imidazolidinyl group, a pyrazolyl group, a pyrazolinyl group, a pyrazolidinyl group, a pyridazinyl group, a pyrazinyl group, a piperidinyl group, a piperazinyl group, a thiolanyl group, a thianyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group and a carbolinyl group; arylvinyl groups such as a styryl group and a naphthylvinyl group; acyl groups such as an acetyl group and a benzoyl group; dialkylamino groups such as a dimethylamino group and a diethylamino group; di-substituted amino groups substituted with an aromatic hydrocarbon group or a condensed polycyclic aromatic group, such as a diphenylamino group and a dinaphthylamino group; diaralkylamino groups such as a dibenzylamino group and a diphenethylamino group; di-substituted amino groups substituted with a heterocyclic group, such as a dipyridylamino group, a dithienylamino group and a dipiperidinyl amino group; dialkenylamino groups such as a diallylamino group; and di-substituted amino groups substituted with a substituent selected from an alkyl group, an aromatic hydrocarbon group, a condensed polycyclic aromatic group, an aralkyl group, a heterocyclic group or an alkenyl group. These substituents may be further substituted with other substituents and may mutually bind via a single bond, an oxygen atom or a sulfur atom to form a ring.

In formula (1), as $R_1$, a "hydrogen atom" or "substituted or unsubstituted aromatic hydrocarbon group" is preferable, and a "hydrogen atom" is particularly preferable.

In formula (1), as $R_2$, a "hydrogen atom" or a "linear or branched alkyl group having 1 to 8 carbon atoms which may have a substituent" is preferable; a "hydrogen atom" or a "linear or branched alkyl group having 1 to 6 carbon atoms which does not have a substituent" is more preferable; a "hydrogen atom" or a "linear or branched alkyl group having 1 to 4 carbon atoms which does not have a substituent" is further preferable; and a "hydrogen atom" or a "methyl group" is particularly preferable.

In formula (1), as $R_3$ to $R_7$, a "hydrogen atom," a "deuterium atom", a "chorine atom," a "cyano group," a "nitro group," a "linear or branched alkyl group having 1 to 8 carbon atoms which may have a substituent," a "linear or branched alkenyl group having 2 to 6 carbon atoms which may have a substituent" or a "linear or branched alkyloxy group having 1 to 8 carbon atoms which may have a substituent" is preferable; a "hydrogen atom," a "chorine atom," a "linear or branched alkyl group having 1 to 6 carbon atoms which does not have a substituent", a "linear or branched alkenyl group having 2 to 4 carbon atoms which does not have a substituent" or a "linear or branched alkyloxy group having 1 to 6 carbon atoms which does not have a substituent" is more preferable; a "hydrogen atom," a "chorine atom," a "linear or branched alkyl group having 1 to 4 carbon atoms which does not have a substituent", a "linear or branched alkenyl group having 2 to 4 carbon atoms which does not have a substituent" or a "linear or branched alkyloxy group having 1 to 4 carbon atoms which does not have a substituent" is particularly preferable.

In formula (1), as V, W, X, Y and Z, the case where all of them are carbon atoms or any one of them is a nitrogen atom is preferable; and the case where V, W, X, Y and Z are all carbon atoms is particularly preferable.

A thiazolidinedione derivative represented by the formula (1) may be a thiazolidinedione derivative represented, for example, by the following formula (1') or the following formula (1").

[Chemical Formula 2]

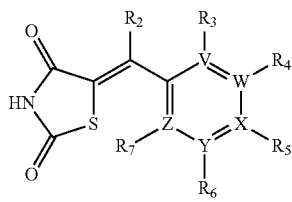

(1')

In formula (1'), $R_2$ represents a hydrogen atom or a linear or branched alkyl group having 1 to 8 carbon atoms which may have a substituent; $R_3$ to $R_7$, which may be identical to or different from each other, represent a hydrogen atom, a deuterium atom, a chlorine atom, a cyano group, a nitro group, a linear or branched alkyl group having 1 to 10 carbon atoms which may have a substituent, a linear or branched alkenyl group having 2 to 6 carbon atoms which may have a substituent, a linear or branched alkyloxy group having 1 to 8 carbon atoms which may have a substituent; $R_3$ to $R_7$ may be joined to each other to form a ring. V, W, X, Y and Z represent a carbon atom or a nitrogen atom; and none or any one of V, W, X, Y and Z is a nitrogen atom which does not have substituents of $R_3$ to $R_7$.

[Chemical Formula 3]

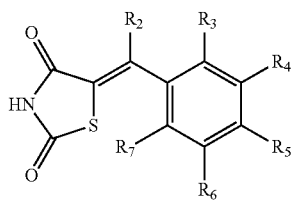

(1")

In formula (1"), $R_2$ represents a hydrogen atom, a linear or branched alkyl group having 1 to 6 carbon atoms which does not have a substituent, $R_3$ to $R_7$, which may be identical to or different from each other, represent a hydrogen atom, a chlorine atom, a linear or branched alkyl group having 1 to 6 carbon atoms which does not have a substituent, a linear or branched alkenyl group having 2 to 4 carbon atoms which does not have a substituent, a linear or branched alkyloxy group having 1 to 6 carbon atoms which does not have a substituent; $R_3$ to $R_7$ may be joined to each other to form a ring.

The charge control agent according to the embodiment is excellent in charge control property, environment resistance and durability. When the charge control agent is used in a grinded toner or a polymerized toner, an image having satisfactory image density, dot reproducibility and thin-line reproducibility without fogging can be obtained.

The thiazolidinedione derivative represented by formula (1) according to the embodiment can be produced by a known method. For example, the thiazolidinedione derivative according to the embodiment can be synthesized by condensing the corresponding N-substituted thiazolidine-2,4-dione with e.g., the corresponding aldehyde or ketone in the presence of a base.

Of the thiazolidinedione derivatives represented by formula (1) according to the embodiment, examples of preferable compounds will be specifically shown below; however, the present invention is not limited to these compounds.

Note that a hydrogen atom is omitted in the following structural formulas.

[Chemical Formula 4]

Exemplary compound 2

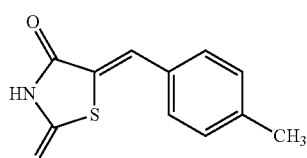

[Chemical Formula 5]

Exemplary compound 3

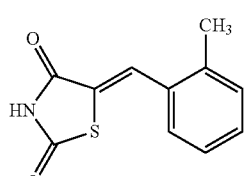

[Chemical Formula 6]

Exemplary compound 4

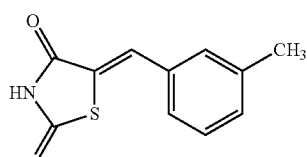

[Chemical Formula 7]

Exemplary compound 5

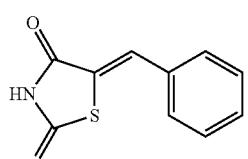

[Chemical Formula 8]

Exemplary compound 6

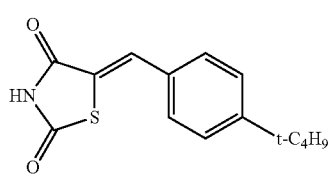

[Chemical Formula 9]

Exemplary compound 7

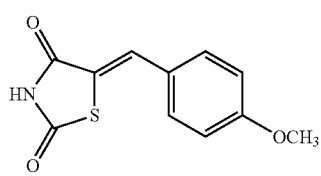

[Chemical Formula 10]

Exemplary compound 8

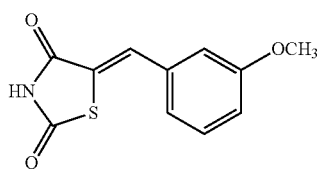

[Chemical Formula 11]

Exemplary compound 9

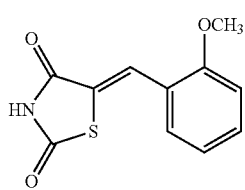

[Chemical Formula 12]

Exemplary compound 10

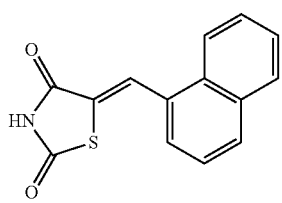

[Chemical Formula 13]

Exemplary compound 11

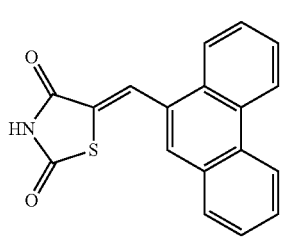

[Chemical Formula 14]

Exemplary compound 12

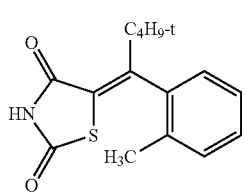

[Chemical Formula 15]

Exemplary compound 13

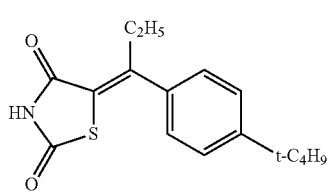

[Chemical Formula 16]

Exemplary compound 14

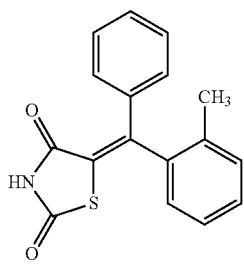

[Chemical Formula 17]

Exemplary compound 15

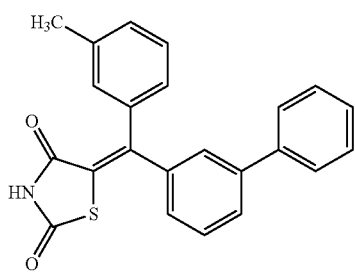

[Chemical Formula 18]

Exemplary compound 16

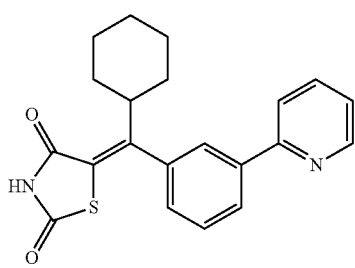

[Chemical Formula 19]

Exemplary compound 17

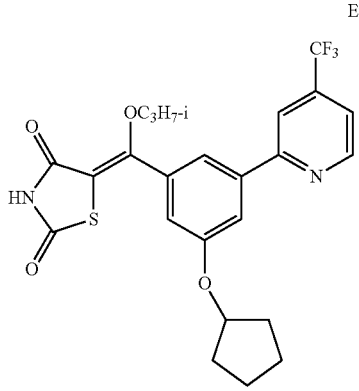

[Chemical Formula 20]

Exemplary compound 18

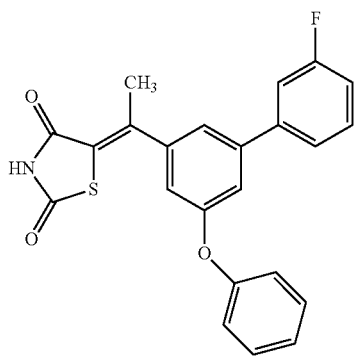

[Chemical Formula 21]

Exemplary compound 19

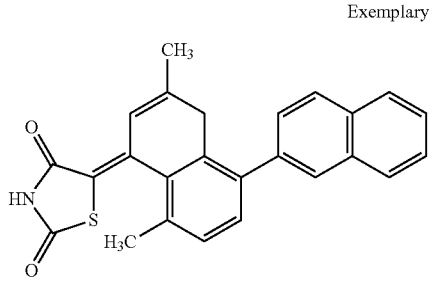

[Chemical Formula 22]

Exemplary compound 20

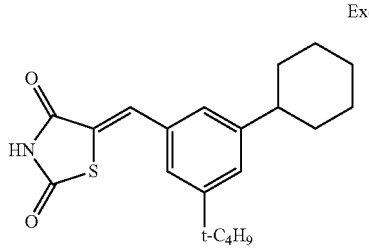

[Chemical Formula 23]

Exemplary compound 21

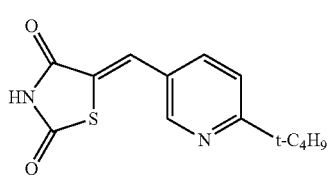

[Chemical Formula 24]

Exemplary compound 22

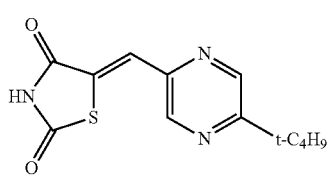

[Chemical Formula 25]

Exemplary compound 23

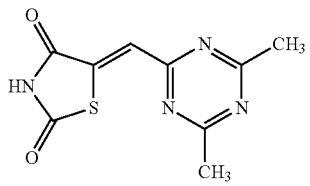

[Chemical Formula 26]

Exemplary compound 24

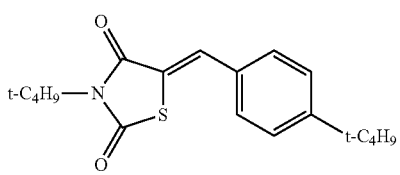

[Chemical Formula 27]

Exemplary compound 25

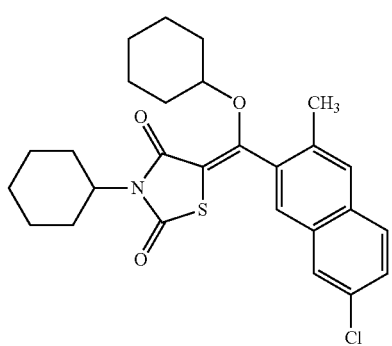

[Chemical Formula 28]

Exemplary compound 26

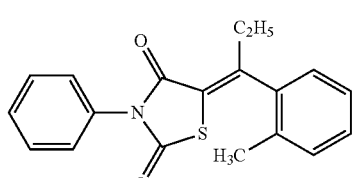

[Chemical Formula 29]

Exemplary compound 27

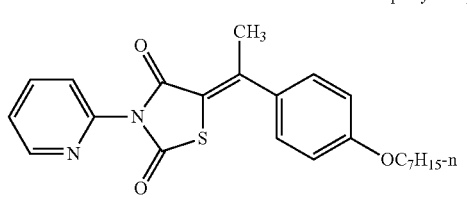

-continued

[Chemical Formula 30]

Exemplary compound 28

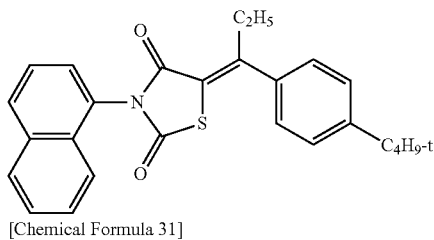

[Chemical Formula 31]

Exemplary compound 29

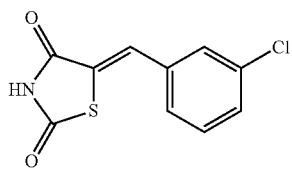

[Chemical Formula 32]

Exemplary compound 30

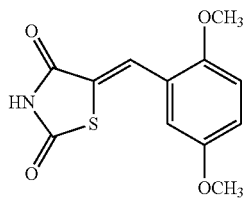

[Chemical Formula 33]

Exemplary compound 31

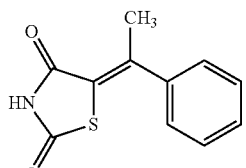

[Chemical Formula 34]

Exemplary compound 32

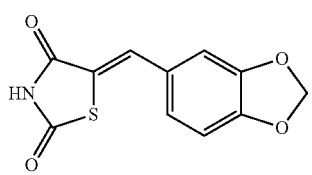

In the embodiment, the charge control agent is preferably used by controlling a volume average particle size to fall within the range of 0.1 to 20 μm and particularly preferably within the range of 0.1 to 10 μm. If the volume average particle size is smaller than 0.1 μm, the amount of charge control agent present on the surface of a toner becomes extremely small, with the result that a desired charge control effect tends not to be obtained. In contrast, if the volume average particle size is larger than 20 μm, the amount of charge control agent falling from a toner increases, with the result that an adverse effect such as contamination within a machine tends to occur, which is not preferable.

Furthermore, when the charge control agent is used in the polymerized toner, the volume average particle size thereof is preferably controlled to be 1.0 μm or less and particularly preferably within the range of 0.01 to 1.0 μm. If the volume average particle size is beyond 1.0 μm, a final electrophotographic toner product has a broad particle-size distribution and free particles are generated, with the result that performance and reliability may decrease. In contrast, if the average particle size falls within the above range, the toner is not only free from the aforementioned drawbacks but also has the following advantages: uneven distribution between toner particles decreases and dispersion among toner particles improves, with the result that variation of performance and reliability becomes small.

Examples of the method for adding the charge control agent according to the embodiment, i.e., a thiazolidinedione derivative, represented by formula (1), to a toner, include an (internal addition) method for previously adding a charge control agent within a toner particle such as a (grinded toner) method in which a charge control agent is added to a binder resin together with a colorant, etc., kneaded and ground, and a (polymerized toner) method of obtaining a polymerized toner by adding a thiazolidinedione derivative represented by formula (1) to a polymerizable monomer and polymerizing them; and an (external addition) method of previously producing a toner particle and then adding the charge control agent to the surface of the toner particle. In the internal addition case, a preferable amount of thiazolidinedione derivative internally added to a toner particle is favorably 0.1 to 10 parts by mass, and more favorably, 0.2 to 5 parts by mass, relative to 100 parts by mass of a binder resin. Furthermore, in the external addition case, a preferable addition amount of thiazolidinedione derivative to a toner particle is favorably 0.01 to 5 parts by mass, and more favorably, 0.01 to 2 parts by mass, relative to 100 parts by mass of a binder resin. Moreover, it is preferable that a thiazolidinedione derivative is fixed to the surface of a toner particle in a mechanochemical manner.

Furthermore, in the embodiment, a charge control agent containing a thiazolidinedione derivative represented by formula (1), as an active substance(s), can be used in combination with another negatively charged charge control agent known in the art. Examples of the preferable charge control agent to be used in combination include an azo based iron complex or a complex salt, an azo based chromium complex or a complex salt, an azo based manganese complex or a complex salt, an azo based cobalt complex or a complex salt, an azo based zirconium complex or a complex salt, a chromium complex of a carboxylic acid derivative or a complex salt, a zinc complex of a carboxylic acid derivative or a complex salt, an aluminum complex of a carboxylic acid derivative or a complex salt and a zirconium complex of a carboxylic acid derivative or a complex salt. As the carboxylic acid derivative, an aromatic hydroxycarboxylic acid is preferable and 3,5-di-tert-butyl salicylic acid is further preferable. Further examples thereof include a boron complex or a complex salt, a negatively charged resin charge control agent.

In the embodiment, in the case where a charge control agent is used in combination with another charge control agent, the addition amount of the charge control agent other than the charge control agent, i.e., a thiazolidinedione derivative represented by formula (1), is preferably 0.1 to 10 parts by mass, relative to 100 parts by mass of a binder resin.

As the binder resin to be used in the toner according to the embodiment, any binder resin can be used as long as it is known in the art. Examples thereof include vinyl polymers prepared by polymerizing a styrene monomer, an acrylate monomer, a methacrylate monomer and the like, copolymers formed of at least two monomers as mention above, a polyester polymer, a polyol resin, a phenol resin, a silicone resin, a polyurethane resin, a polyamide resin, a furan resin, an epoxy resin, a xylene resin, a terpene resin, a coumaronein-dene resin, a polycarbonate resin and a petroleum resin.

Examples of the styrene monomer, acrylate monomer and methacrylate monomer for constituting the vinyl polymer or the copolymer will be described below; however, they are not limited to the following examples.

Examples of the styrene monomer include styrenes such as styrene, o-methylstyrene, m-methylstyrene, p-methylstyrene, p-phenylstyrene, p-ethylstyrene, 2,4-dimethylstyrene, p-n-amylstyrene, p-tert-butyl styrene, p-n-hexylstyrene, p-n-octylstyrene, p-n-nonylstyrene, p-n-decylstyrene, p-n-dodecylstyrene, p-methoxystyrene, p-chlorostyrene, 3,4-dichlorostyrene, m-nitrostyrene, o-nitrostyrene and p-nitrostyrene or derivatives thereof.

Examples of the acrylate monomer include acrylic acid or esters thereof such as methyl acrylate, ethyl acrylate, propyl acrylate, n-butyl acrylate, isobutyl acrylate, n-octyl acrylate, n-dodecyl acrylate, 2-ethylhexyl acrylate, stearyl acrylate, 2-chlorethyl acrylate and phenyl acrylate.

Examples of the methacrylate monomer include methacrylic acid or esters thereof such as methyl methacrylate, ethyl methacrylate, propyl methacrylate, n-butyl methacrylate, isobutyl methacrylate, n-octyl methacrylate, n-dodecyl methacrylate, 2-ethylhexyl methacrylate, stearyl methacrylate, phenyl methacrylate, dimethylaminoethyl methacrylate and diethylaminoethyl methacrylate.

Examples of other monomers forming the vinyl polymer or copolymer include the following (1) to (18): (1) monoolefins such as ethylene, propylene, butylene and isobutylene; (2) polyenes such as butadiene and isoprene; (3) vinyl halides such as vinyl chloride, vinylidene chloride, vinyl bromide and vinyl fluoride; (4) vinyl esters such as vinyl acetate, vinyl propionate and vinyl benzoate; (5) vinyl ethers such as vinyl methyl ether, vinyl ethyl ether and vinyl isobutyl ether; (6) vinyl ketones such as vinyl methyl ketone, vinyl hexyl ketone and methyl isopropenyl ketone; (7) N-vinyl compounds such as N-vinyl pyrrole, N-vinyl carbazole, N-vinyl indole and N-vinyl pyrrolidone; (8) vinyl naphthalenes; (9) acrylic acid or methacrylic acid derivatives such as acrylonitrile, methacrylonitrile and acrylic amide; (10) unsaturated dibasic acids such as maleic acid, citraconic acid, itaconic acid, alkenylsuccinic acid, fumaric acid and mesaconic acid; (11) unsaturated dibasic acid anhydrides such as maleic acid anhydride, citraconic acid anhydride, itaconic acid anhydride and alkenyl succinic acid anhydride; (12) monoesters of unsaturated dibasic acids such as a monomethyl ester of maleic acid, a monoethyl ester of maleic acid, a monobutyl ester of maleic acid, a monomethyl ester of citraconic acid, a monoethyl ester of citraconic acid, a monobutyl ester of citraconic acid, a monomethyl ester of itaconic acid, a monomethyl ester of alkenyl succinic acid, a monomethyl ester of fumaric acid and a monomethylester of mesaconic acid; (13) unsaturated dibasic acid esters such as dimethyl maleate and dimethyl fumarate; (14) α,β-unsaturated acids such as crotonic acid and cinnamic acid; (15) α,β-unsaturated acid anhydrides such as crotonic acid anhydride and cinnamic acid anhydride; (16) monomers having a carboxyl group such as anhydrides of the α,β-unsaturated acid mentioned above and a lower fatty acid, alkenylmalonic acid, alkenylglutaric acid, alkenyladipic acid, anhydrides of these and monoester of these; (17) hydroxyalkyl acrylate acids or methacrylates such as 2-hydroxyethyl acrylate, 2-hydroxyethyl methacrylate and 2-hydroxypropyl methacrylate; and (18) monomers having a hydroxy group such as 4-(1-hydroxy-1-methylbutyl)styrene and 4-(1-hydroxy-1-methylhexyl)styrene.

In the toner according to the embodiment, the vinyl polymer or copolymer of a binder resin may have a crosslinked structure bridged by a crosslinking agent having two or more vinyl groups. Examples of the crosslinking agent used herein include aromatic divinyl compounds such as divinyl benzene and divinyl naphthalene. Examples of diacrylate compounds connected with an alkyl chain include ethylene glycol diacrylate, 1,3-butylene glycol diacrylate, 1,4-butanediol diacrylate, 1,5-pentanediol diacrylate, 1,6-hexane diol diacrylate, neopentyl glycol diacrylate or compounds obtained by substituting acrylates of the above compounds with methacrylates.

Examples of the diacrylate compounds connected with an alkyl chain containing an ether bond include diethylene glycol diacrylate, triethylene glycol diacrylate, tetraethylene glycol diacrylate, polyethylene glycol #400 diacrylate, polyethylene glycol #600 diacrylate, dipropylene glycol diacrylate or compounds obtained by substituting acrylates of the above compounds with methacrylates.

Further examples include a diacrylate compound or a dimethacrylate compound connected with a chain containing an aromatic group and an ether bond. As polyester type diacrylates, for example, trade name, MANDA (manufactured by Nippon Kayaku Co., Ltd.) may be mentioned.

Examples of a polyfunctional crosslinking agent include pentaerythritol triacrylate, trimethylolethane triacrylate, trimethylolpropane triacrylate, tetramethylolmethane tetraacrylate, oligo ester acrylate and compounds obtained by substituting acrylates of the above compounds with methacrylates, triallyl cyanurate and triallyl trimellitate.

These crosslinking agents are preferably used in an amount of 0.01 to 10 parts by mass, relative to 100 parts by mass of other monomer components and particularly preferably in an amount of 0.03 to 5 parts by mass. Of these crosslinkable monomers, aromatic divinyl compounds (particularly preferably divinyl benzene) and diacrylate compounds connected with a binding chain containing a single aromatic group and a single ether bond are preferably used in view of fixability to a toner resin and offset resistance. Of these, combinations of monomers capable of forming a styrene copolymer and a styrene-acrylic copolymer, are preferable.

In the embodiment, examples of the polymerization initiator to be used in producing a vinyl polymer or a copolymer include 2,2'-azobisisobutyronitrile, 2,2'-azobis(4-methoxy-2,4-dimethylvaleronitrile), 2,2'-azobis(2,4-dimethylvaleronitrile), 2,2'-azobis(2-methylbutyronitrile), dimethyl-2,2'-azobis isobutyrate, 1,1'-azobis(1-cyclohexanecarbonitrile), 2-(carbamoylazo)-isobutyronitrile, 2,2'-azobis(2,4,4-trimethylpentane), 2-phenylazo-2',4'-dimethyl-4'-methoxyvaleronitrile, 2,2'-azobis(2-methylpropane), ketone peroxides such as methyl ethyl ketone peroxide, acetyl acetone peroxide and cyclohexanone peroxide, 2,2-bis(tert-butyl peroxy)butane, tert-butyl hydroperoxide, cumene hydroperoxide, 1,1,3,3-tetramethylbutyl hydroperoxide, di-tert-butyl peroxide, tert-butylcumyl peroxide, dicumyl peroxide, α-(tert-butyl peroxy)isopropyl benzene, isobutyl peroxide, octanoyl peroxide, decanoyl peroxide, lauroyl peroxide, 3,5,5-trimethylhexanoyl peroxide, benzoyl peroxide, m-tolyl peroxide, diisopropylperoxy dicarbonate, di-2-ethylhexylperoxy dicarbonate, di-n-propylperoxy dicarbonate, di-2-ethoxyethylperoxy carbonate, diethoxyisopropylperoxy dicarbonate, bis(3-methyl-3-methoxybutyl)peroxy carbonate, acetylcyclohexylsulfonyl peroxide, tert-butylperoxy acetate, tert-butylperoxy isobutyrate, tert-butylperoxy-2-ethyl hexanoate, tert-butylperoxy laurate, tert-butyloxy benzoate, tert-butylperoxyisopropyl carbonate, di-tert-butylperoxy isophthalate, tert-butylperoxyallyl carbonate, isoamylperoxy-2-ethyl hexanoate, di-tert-butylperoxyhexahydro terephthalate and tert-butylperoxy azelate.

In the case where the binder resin is a styrene-acrylate resin, when a molecular weight distribution of a component of the resin soluble in tetrahydrofuran (hereinafter, simply referred to as THF) is obtained by gel permeation chromatography (hereinafter, simply referred to as GPC), it is preferable that at least one peak is present in the range of a molecular weight of 3,000 to 50,000 (in terms of number average molecular weight) and at least one peak is present within the range of a molecular weight of 100,000 or more, in view of fixability, offset property and storage stability. Furthermore, a binder resin having a THF soluble matter which contains a component of a molecular weight of 100,000 or less in an amount of 50 to 90% in the molecular weight distribution is preferable. The binder resin is further preferably to have a main peak present in the range of a molecular weight of 5,000 to 30,000 and most preferably 5,000 to 20,000.

In the case where the binder resin is a vinyl polymer such as a styrene-acrylate resin, its acid value is preferably 0.1 mg KOH/g to 100 mg KOH/g, further preferably, 0.1 mg KOH/g to 70 mg KOH/g, and further preferably 0.1 mg KOH/g to 50 mg KOH/g.

As the monomer constituting a polyester polymer, the following monomers are mentioned.

Examples of a divalent alcohol component include ethylene glycol, propylene glycol, 1,3-butanediol, 1,4-butanediol, 2,3-butanediol, diethylene glycol, triethylene glycol, 1,5-pentanediol, 1,6-hexane diol, neopentyl glycol, 2-ethyl-1,3-hexanediol, hydrogenated bisphenol A or a diol obtained by polymerizing a cyclic ether such as ethylene oxide and propylene oxide with bisphenol A.

To crosslink a polyester resin, an alcohol of a trivalence or larger is preferably used in combination. Examples of the polyhydric alcohol of a trivalence or larger include sorbitol, 1,2,3,6-hexanetetrole, 1,4-sorbitane, pentaerythritol, dipentaerythritol, tripentaerythritol, 1,2,4-butanetriol, 1,2,5-pentatriol, glycerol, 2-methylpropanetriol, 2-methyl-1,2,4-butanetriol, trimethylol ethane, trimethylol propane and 1,3,5-trihydroxybenzene.

Examples of an acid component for forming the polyester polymer include benzenedicarboxylic acids such as phthalic acid, isophthalic acid and terephthalic acid or anhydrides thereof; alkyldicarboxylic acids such as succinic acid, adipic acid, sebacic acid and azelaic acid or anhydride thereof; unsaturated dibasic acids such as maleic acid, citraconic acid, itaconic acid, alkenylsuccinic acid, fumaric acid and mesaconic acid; unsaturated dibasic acid anhydrides such as maleic acid anhydride, citraconic acid anhydride, itaconic acid anhydride and alkenylsuccinic acid anhydride. Furthermore, examples of polyvalent carboxylic acid component of trivalence or larger include trimellitic acid, pyromellitic acid, 2,5,7-naphthalenetricarboxylic acid, 1,2,4-naphthalenetricarboxylic acid, 1,2,4-butanetricarboxylic acid, 1,2,5-hexanetricarboxylic acid, 1,3-dicarboxy-2-methyl-2-methylenecarboxy propane, tetra(methylenecarboxy)methane, 1,2,7,8-octanetetracarboxylic acid, EnPol trimer acid or anhydrides of these, and a partial lower alkyl ester.

In the case where the binder resin is a polyester resin, when a molecular weight distribution of a THF soluble resin component is obtained, it is preferable that at least one peak is present in the range of a molecular weight of 3,000 to 50,000 in view of fixability and offset resistance of a toner. A binder resin preferably contains a THF soluble component having a molecular weight of 100,000 or less in an amount of 60 to 100%. It is further preferable that at least one peak is present within the range of a molecular weight of 5,000 to 20,000.

In the embodiment, the molecular weight distribution of a binder resin is measured by GPC using THF as a solvent. The molecular weight above is the standard polystyrene equivalent number average molecular weight, which was measured, for example, by an HLC-8220 GPC apparatus (manufactured by Tosoh Corporation).

In the case where the binder resin is a polyester resin, its acid value is preferably 0.1 mg KOH/g to 100 mg KOH/g, further preferably 0.1 mg KOH/g to 70 mg KOH/g, and further preferably 0.1 mg KOH/g to 50 mg KOH/g.

Furthermore, a hydroxyl value is preferably 30 mg KOH/g or less and further preferably 10 mg KOH/g to 25 mg KOH/g.

In the embodiment, an amorphous polyester resin and two or more crystalline polyester resins may be used in combination. In this case, materials are preferably selected in consideration of compatibility of each material.

As the amorphous polyester resin, one synthesized from a polyvalent carboxylic acid component, preferably an aromatic polyvalent carboxylic acid, and a polyhydric alcohol component is preferably used.

As the crystalline polyester resin, one synthesized from a divalent carboxylic acid component, preferably an aliphatic dicarboxylic acid, and a divalent alcohol component is suitably used.

As the binder resin to be used in the toner according to the embodiment, a resin containing a monomer component that can react with both vinyl polymer component and/or polyester resin component, in these resin components can be also used. Of the monomers constituting a polyester resin component, examples of a monomer that can react with a vinyl polymer include unsaturated dicarboxylic acids such as phthalic acid, maleic acid, citraconic acid and itaconic acid or anhydrides thereof. Examples of the monomer constituting a vinyl polymer component include monomers having a carboxyl group or a hydroxy group, or acrylic acid or methacrylates.

Furthermore, in the case where a polyester polymer, a vinyl polymer and other binder resins are used in combination, the binder resins which give an acid value of 0.1 to 50 mg KOH/g, as a whole, are preferably contained in an amount of 60 mass % or more.

In the embodiment, the acid value of a binder resin component of a toner composition is obtained by the following method. The basic operation follows JIS K-0070.

(1) A sample is used after additives except a binder resin (polymer component) are removed. Alternatively, acid values and contents of components except a binder resin and a crosslinked binder resin are pre-determined. The ground product of the sample (0.5 to 2.0 g) is weighed and the weight of the polymer component is defined as W g. For example, when the acid value of the binder resin is measured directly from a toner, the acid values and contents of e.g. a colorant or a magnetic substance have been separately measured, and the acid value of the binder resin is calculated.

(2) The sample is placed in a 300 (ml) beaker and dissolved by adding 150 (ml) of toluene/ethanol (volume ratio 4/1) solution mixture.

(3) Titration is performed by use of a 0.1 mol/L KOH ethanol solution and a potential difference titration apparatus.

(4) Use amount of KOH solution at this time is defined as S (ml). Simultaneously, a blank is measured and the use amount of KOH solution at this time is defined as B (ml). The acid value is calculated in accordance with the following formula (1). Note that, f represents a factor of KOH concentration.

$$\text{Acid value(mg KOH/g)} = [(S-B) \times f \times 5.61]/W \quad (1)$$

The binder resin of a toner and a composition containing the binder resin have a glass transition temperature (Tg) of preferably 35 to 80° C. and particularly preferably 40 to 75°

C., in view of toner storage stability. If Tg is lower than 35° C., a toner tends to deteriorate under a high temperature atmosphere and offset tends to occur during the fixation process. In contrast, if Tg is beyond 80° C., fixability tends to reduce.

In the polymerized toner of the embodiment, a binder resin having a softening point within the range of 80 to 140° C. is preferably used. If the softening point of a binder resin is less than 80° C., stability of a toner after fixation and during storage and stability of a toner image may deteriorate. On the other hand, if a softening point is beyond 140° C., low-temperature fixability may deteriorate.

Examples of the magnetic substance according to the embodiment include (1) magnetic oxides of iron such as magnetite, maghemite and ferrite and iron oxides containing another metal oxide. Alternatively, examples thereof include (2) metals such as iron, cobalt and nickel or alloys of these metals with metals such as aluminum, cobalt, copper, lead, magnesium, tin, zinc, antimony, beryllium, bismuth, cadmium, calcium, manganese, selenium, titanium, tungsten and vanadium and (3) a mixture of these.

Specific examples of the magnetic substance include $Fe_3O_4$, $\gamma\text{-}Fe_2O_3$, $ZnFe_2O_4$, $Y_3Fe_5O_{12}$, $CdFe_2O_4$, $Gd_3Fe_5O_{12}$, $CuFe_2O_4$, $PbFe_{12}O$, $NiFe_2O_4$, $NdFe_2O$, $BaFe_{12}O_{19}$, $MgFe_2O_4$, $MnFe_2O_4$, $LaFeO_3$, iron powder, cobalt powder and nickel powder. The aforementioned magnetic substances are used singly or in combination with two or more. Particularly preferable magnetic substance is fine powder of triiron tetroxide or $\gamma$-iron sesquioxide.

Furthermore, magnetic oxides of iron such as magnetite, maghemite, ferrite containing a xenogeneic element or a mixture of these can be also used. Examples of the xenogeneic element include lithium, beryllium, boron, magnesium, aluminum, silicon, phosphorus, germanium, zirconium, tin, sulfur, calcium, scandium, titanium, vanadium, chromium, manganese, cobalt, nickel, copper, zinc and gallium. A preferable xenogeneic element is selected from magnesium, aluminum, silicon, phosphorus or zirconium. The xenogeneic element may be incorporated in an iron oxide crystal lattice or in iron oxide as an oxide, or may be present on the surface as an oxide or a hydroxide; however, a xenogeneic element is preferably contained as an oxide.

The xenogeneic elements each can be incorporated into a particle by mixing a salt of a xenogeneic element in producing a magnetic substance and by adjusting pH. Alternatively, after a magnetic substance particle is produced, pH is adjusted or a salt of each element is added to adjust pH, thereby precipitating a xenogeneic element on the surface of the particle.

The use amount of the magnetic substance as mentioned above is preferably 10 to 200 parts by mass and more preferably 20 to 150 parts by mass relative to 100 parts by mass of a binder resin. The number average particle size of the magnetic substance is preferably 0.1 to 2 μm and more preferably 0.1 to 0.5 μm. The number average particle size can be obtained by taking a photograph of images of particles magnified by a transmission electron microscope, and measuring the diameters by a digitizer.

Furthermore, as to magnetic properties of a magnetic substance, when 10K oersteds are applied, a magnetic substance preferably has magnetic properties: a coercive force of 20 to 150 oersteds, a saturation magnetization of 50 to 200 emu/g and a residual magnetization of 2 to 20 emu/g.

The magnetic substance can be also used as a colorant. As the colorant for a black toner according to the embodiment, black or blue dye or pigment particle may be mentioned. Examples of the black or blue pigments include carbon black, aniline black, acetylene black, phthalocyanine blue and indanthrene blue. Examples of the black or blue dye also include an azo-based dye, an anthraquinone-based dye, a xanthene-based dye and a methine-based dye.

In the case where the magnetic substance is used as a color toner, the following substances are used as a colorant. As a magenta colorant, a condensed azo compound, a diketo-pyrrolo-pyrrole compound, an anthraquinone compound, a quinacridone compound, a basic dye, a lake dye, a naphthol dye, a benzimidazolone compound, a thioindigo compound and a perylene compound are used. Specific examples of a magenta colorant belonging to a pigment include C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207 and 209; C.I. pigment Violet 19 and C.I. Vat Red 1, 2, 10, 13, 15, 23, 29 and 35.

The pigments mentioned above may be used singly; however, these pigments are each preferably used in combination with a dye to improve definition in view of quality of a full color image.

Examples of a magenta colorant belonging to a dye include oil soluble dyes such as C.I. Solvent Red 1, 3, 8, 23, 24, 25, 27, 30, 49, 81, 82, 83, 84, 100, 109 and 121, C.I. Disperse Red 9, C.I. Solvent Violet 8, 13, 14, 21 and 27 and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39 and 40 and C.I. Basic Violet 1, 3, 7, 10, 14, 15, 21, 25, 26, 27 and 28.

As a cyan colorant, a copper phthalocyanine compound and a derivative thereof, anthraquinone and a basic dye lake compound can be used. Specific examples of the cyan colorant belonging to a pigment include C.I. Pigment Blue 2, 3, 15, 16, 17, C.I. Vat Blue 6, C.I. Acid Blue 45 or a copper phthalocyanine pigment having a phthalocyanine skeleton having 1 to 5 phthalimide methyl group substituted.

As a yellow colorant, a condensed azo compound, an isoindolinone compound, an anthraquinone compound, an azo metal complex, a methine compound or an allyl amide compound is used. Specific examples of the yellow pigment include C.I. Pigment Yellow 1, 2, 3, 4, 5, 6, 7, 10, 11, 12, 13, 14, 15, 16, 17, 23, 65, 73 and 83 and C.I. Vat Yellow 1, 3 and 20.

Examples of an orange pigment include red/yellow lead, molybdenum orange, permanent orange GTR, pyrazolone orange, Vulcan orange, benzidine orange G, indanthrene brilliant orange RK, and indanthrene brilliant orange GK. Examples of a violet pigment include manganese violet, fast violet B and methyl violet lake. Examples of a green pigment include chromium oxide, chromium green, pigment green, malachite green lake, final yellow green G. Examples of a white pigment include zinc oxide, titanium oxide, antimony white and zinc sulfate.

The use amount of colorant is preferably 0.1 to 20 parts by mass relative to 100 parts by mass of a binder resin.

The toner of the embodiment may be blended with a carrier and used as a two-component developer. As the carrier to be used in the embodiment, not only a general carrier such as ferrite and magnetite but also a resin-coated carrier can be used.

The resin-coated carrier is formed of a carrier core particle and a coating material of a resin coating the surface of the carrier core particle. Preferable examples of the resin to be used as the coating material include styrene-acrylate resins such as a styrene-acrylate copolymer and a styrene-methacrylate copolymer, an acrylate resin such as an acrylate copolymer and a methacrylate copolymer, fluorine-containing resins such as polytetrafluoroethylene, monochlorotrifluoroethylene polymer and polyvinylidene fluoride, a silicone resin, a polyester resin, a polyamide resin, a polyvinyl butyral and an amino acrylate resin. Other than these, any resin such as an ionomer resin and a polyphenylene sulfide resin may be used as long as it can be used as a coating material for a carrier. These resins can be used singly or in combination.

Furthermore, a binder type carrier core having magnetic powder dispersed in a resin can be used. In the case of a resin-coated carrier, as a method for coating the surface of a carrier core with at least resin coating material, a method in which a resin is dissolved or suspended in a solvent and applied to a carrier core or a method in which a resin is mixed in a powder state can be used. The ratio of a resin coating material to a resin-coated carrier may be appropriately determined; however, the ratio may be preferably 0.01 to 5 mass % and more preferably 0.1 to 1 mass % relative to the resin-coated carrier.

When a magnetic substance is coated with a coating material consisting of a mixture of two or more components, examples of practical cases thereof include:
(1) a case where a mixture (12 parts by mass) containing dimethyldichloro silane and dimethylsilicon oil (in a mass ratio of 1:5) is applied to a titanium oxide fine-powder particle (100 parts by mass); and
(2) a case where a mixture (20 parts by mass) containing dimethyldichloro silane and dimethyl silicon oil (in a mass ratio of 1:5) is applied to a silica fine-powder particle (100 parts by mass).

Of the above resins, a styrene-methyl methacrylate copolymer, a mixture of fluorine-containing resin and a styrene copolymer or a silicone resin is preferably used, and a silicone resin is particularly preferable.

Examples of the mixture of a fluorine-containing resin and a styrene copolymer include a mixture of polyvinylidene fluoride and a styrene-methyl methacrylate copolymer, a mixture of polytetrafluoroethylene and a styrene-methyl methacrylate copolymer and a mixture of a vinylidene fluoride-tetra fluoroethylene copolymer (copolymer mass ratio: 10:90 to 90:10), a styrene-2-ethylhexyl acrylate copolymer (copolymer mass ratio: 10:90 to 90:10) and a styrene-2-ethylhexyl acrylate-methyl methacrylate copolymer (copolymer mass ratio: 20-60:5-30:10:50).

As a silicone resin, a modified silicone resin is mentioned, which is produced by reacting a nitrogen-containing silicone resin, a nitrogen-containing silane coupling agent and a silicone resin.

As the carrier core magnetic material, oxides such as ferrite, iron-excessive ferrite, magnetite and γ-iron oxide and metals such as iron, cobalt and nickel or alloys of these can be used. Examples of elements contained in the these magnetic material include iron, cobalt, nickel, aluminum, copper, lead, magnesium, tin, zinc, antimony, beryllium, bismuth, calcium, manganese, selenium, titanium, tungsten and vanadium. Preferable examples of the elements include a copper-zinc-iron based ferrite containing copper, zinc and iron as main components and a manganese-magnesium-iron based ferrite containing manganese, magnesium and iron as main components.

The resistance value of a carrier is preferably set to $10^6$ to $10^{10}$ Ωcm by controlling a degree of unevenness of a carrier surface and the amount of coating resin. As the particle size of a carrier, 4 to 200 μm is acceptable. The particle size is preferably 10 to 150 μm and more preferably 20 to 100 μm. Particularly, a resin-coated carrier preferably has a 50% particle size of 20 to 70 μm.

In the two-component developer, the toner of the embodiment is preferably used in an amount of 1 to 200 parts by mass relative to 100 parts by mass of a carrier and more preferably, in an amount of 2 to 50 parts by mass relative to 100 parts by mass of a carrier.

The toner of the embodiment may further contain wax. Examples of the wax to be used in the embodiment include aliphatic hydrocarbon waxes such as a low molecular weight polyethylene, a low molecular weight polypropylene, a polyolefin wax, a microcrystalline wax, a paraffin wax and Sasol-wax; oxides of aliphatic hydrocarbon waxes such as polyethylene oxide wax or block copolymers thereof; vegetable waxes such as candelilla wax, Carnauba wax, Japanese wax and jojoba wax; animal waxes such as Beeswax, lanoline and spermaceti; mineral waxes such as ozocerite, ceresin and petrolatum; waxes containing a fatty acid ester as a main component such as montanic acid ester wax and castor wax; and waxes such as deoxidized Carnauba wax, obtained by partly or wholly deoxidizing a fatty acid ester.

Other examples of the waxes include saturated linear fatty acids such as palmitic acid, stearic acid, montanic acid or further a linear alkyl carboxylic acid having a linear alkyl group; unsaturated fatty acids such as planjin acid, eleostearic acid and barinaric acid; saturated alcohols such as stearyl alcohol, eicosyl alcohol, behenyl alcohol, carnaupyl alcohol, ceryl alcohol, mesilyl alcohol or a long-chain alkyl alcohol; polyhydric alcohols such as sorbitol; fatty acid amides such as linoleic acid amide, olefin acid amide and lauric acid amide; saturated fatty acid bisamides such as methylenebis capric acid amide, ethylenebis lauric acid amide and hexamethylenebis stearic acid amide; unsaturated fatty acid amides such as ethylenebis oleic acid amide, hexamethylenebis oleic acid amide, N,N'-dioleyladipic acid amide and N,N'-dioleylsepacic acid amide; aromatic bisamides such as m-xylenebis stearic acid amide and N,N'-distearyl isophthalic acid amide; fatty acid metal salts such as calcium stearate, calcium laurate, zinc stearate and magnesium strearate; waxes obtained by grafting a vinyl monomer such as styrene and acrylate to an aliphatic hydrocarbon wax; partially esterified compounds obtained by a reaction of a fatty acid such as behenic acid monoglyceride and a polyhydric alcohol; and methyl ester compounds having a hydroxyl group obtained by hydrogenating a vegetable oil.

Examples of waxes preferably used include polyolefins prepared by radical polymerization of an olefin under high pressure; polyolefins prepared by purifying a low molecular weight by-product obtained during a polymerization process of a high molecular weight polyolefin; polyolefins obtained by polymerization in the presence of a catalyst such as a Ziegler catalyst and a metallocene catalyst under low pressure; polyolefins obtained by polymerization using radiation, electromagnetic wave or light; low molecular weight polyolefins obtained by thermolysis of a high molecular weight polyolefin; paraffin wax, microcrystalline wax, a Fischer-Tropsch wax; synthesized hydrocarbon wax prepared by synthesis in accordance with e.g., Synthol method, Hydrocoal method and Arge method; synthetic waxes using a compound having a single carbon atom as a monomer; hydrocarbon waxes having a functional group such as a hydroxy group or a carboxyl group; a mixture of a hydrocarbon wax and a hydrocarbon wax having a functional group; and graft modified waxes prepared by modifying these waxes as a base with a vinyl monomer such as styrene, a maleate, an acrylate, a methacrylate and a maleic acid anhydride.

Furthermore, waxes treated in a press-sweating process, a solvent process, a recrystallization process, a vacuum distillation process, a supercritical gas extraction process or a solution crystallization process to narrow a molecular weight distribution, and waxes, from which a low molecular weight solid fatty acid, a low molecular weight solid alcohol, a low molecular weight solid compound and other impurities are removed, are preferably used.

The wax to be used in the embodiment preferably has a melting point of 50 to 140° C. in order to keep balance between fixability and offset resistance, and further preferably 70 to 120° C. If the melting point is less than 50° C., blocking resistance tends to reduce. In contrast, if the melting point is beyond 140° C., it is difficult to exert an offset resistance effect.

Furthermore, if different types (two or more) of waxes are used in combination, plasticizing action and mold release action (actions of wax) can be simultaneously exerted.

Examples of types of waxes having a plasticizing action include a wax having a low melting point or a wax having a branch in the molecular structure and a polar group. Examples of waxes having a mold release action include waxes having a high melting point and waxes having a linear structure and nonpolar waxes having no functional group. Practical examples include a combination of different types (two or more) of waxes whose melting points differ by 10° C. to 100° C. and a combination of a polyolefin and graph-modified polyolefin.

When two waxes selected have the same structure, wax having a relatively lower melting point exerts a plasticizing action, whereas a wax having a higher melting point exerts a mold release action. At this time, if the difference between melting points is 10 to 100° C., a functional separation can be efficiently exerted. If the difference is less than 10° C., it is difficult to exert a functional separation effect. If the difference is beyond 100° C., it is difficult to obtain emphasis of actions due to interaction. In this case, at least one of waxes preferably has a melting point of 70 to 120° C. and further preferably, 70 to 100° C. This is because functional separation effect tends to be exerted.

Furthermore, a wax having a branched structure, a wax having a polar group such as a functional group and a wax modified with a component different from a main component relatively exert a plasticization action; whereas, a wax having a linear structure, a nonpolar wax having no functional group and a plain wax unmodified relatively exert a mold release action. Examples of preferable combinations include a combination of a polyethylene homopolymer or copolymer containing ethylene as a main component and a polyolefin homopolymer or copolymer containing an olefin except ethylene as a main component; a combination of a polyolefin and a graft-modified polyolefin; a combination of an alcohol wax, a fatty acid wax or an ester wax and a hydrocarbon wax; a combination of a Fischer-Tropsch wax or a polyolefin wax and a paraffin wax or a microcrystal wax; a combination of a Fischer-Tropsch wax and a porlyolefin wax; a combination of a paraffin wax and a microcrystal wax; and a combination of Carnauba wax, candelilla wax, rice wax or a montan wax and a hydrocarbon wax.

In any one of the cases, when an endothermic peak of a toner is observed by DSC, a peak top temperature of a maximum peak is preferably present in the range of 70 to 110° C. and a maximum peak is further preferably present in the range of 70 to 110° C. By virtue of this, storage stability and fixability of the toner can be easily balanced.

In the toner of the embodiment, it is effective to use these waxes in the total content of preferably 0.2 to 20 parts by mass relative to 100 parts by mass of a binder resin and further preferably 0.5 to 10 parts by mass.

In the embodiment, the melting point of a wax is defined as the peak top temperature of the maximum peak of endothermic peak of a wax determined by DSC.

In the embodiment, DSC of a wax or a toner is preferably determined by a differential scanning calorimeter of a highly accurate internal heating/input compensation system. Measurement is performed in accordance with the method defined in ASTM D 3418-82. The DSC curve to be used in the embodiment is obtained, after the temperature is increased and decreased to remove history, by increasing the temperature at an increase rate of 10° C./min.

To the toner of the embodiment, a flowability improver may be added. The flowability improver is added to the surface of a toner, thereby improving flowability of the toner (making the toner easily flow). Examples of the flowability improver include carbon black, fluorine resin powders such as a vinylidene fluoride fine powder and a polytetrafluoroethylene fine powder, fine-powder silica such as silica produced by a wet-process and silica produced by a dry-process, a fine powder titanium oxide, fine-powder alumina, and processed silica which is obtained by treating the surface of these with a silane coupling agent, a titanium coupling agent or silicone oil, such as processed silica, processed titanium oxide and processed alumina. Of them, fine powder silica, fine powder titanium oxide and fine powder alumina are preferable. Furthermore, processed silica obtained by treating the surface of these with a silane coupling agent or silicone oil is further preferable. The particle size of the flowability improver is preferably 0.001 to 2 μm in terms of average primary particle size and particularly preferably 0.002 to 0.2 μm.

Preferable fine powder silica is one produced by vapor phase oxidation of a silicon halide compound, called dry-process silica or fumed silica.

Examples of commercially available silica fine powder produced by vapor phase oxidation of a silicon halide compound include ones sold under the following trade names: AEROSIL (manufactured by Nippon Aerosil Co., Ltd., the same shall apply hereinafter) -130, -300, -380, -TT600, -MOX170, -MOX80, -COK84; Ca—O—SiL (manufactured by CABOT Corporation, the same shall apply hereinafter) -M-5, -MS-7, -MS-75, -HS-5, -EH-5; Wacker HDK (manufactured by WACKER-CHEMIE GMBH, the same shall apply hereinafter) -N20 V15, -N20E, -T30, -T40; and D-C Fine Silica (manufactured by Dow Corning Incorporated): Fransol (manufactured by Fransil).

Furthermore, a processed silica fine-powder particle, which is a silica fine-powder particle produced by vapor phase oxidation of a silicon halide compound and treated with a hydrophobic treatment, is more preferable. In the processed silica fine-powder particle, a silica fine-powder particle treated so as to have a degree of hydrophobicity (measured by a methanol titration test) of preferably 30 to 80% is particularly preferable. Hydrophobicity is imparted by a chemical or physical treatment with an organic silicon compound or the like capable of reacting with or physically adsorbing to a silica fine-powder particle. As a preferable method, a silica fine-powder particle, (which is produced by vapor phase oxidation of a silicon halide compound) is treated with an organic silicon compound.

Examples of the organic silicon compound include hydroxypropyltrimethoxysilane, phenyltrimethoxysilane, n-hexadecyltrimethoxysilane, n-octadecyltrimethoxysilane, vinylmethoxysilane, vinyltriethoxysilane, vinyltriacetoxysilane, dimethylvinylchlorosilane, divinylchlorosilane, γ-methacryloxypropyltrimethoxysilane, hexamethyldisilane, trimethylsilane, trimethylchlorosilane, dimethyldichlorosilane, methyltrichlorosilane, allyldimethylchlorosilane, allylphenyldichlorosilane, benzyldimethylchlorosilane, bromomethyldimethylchlorosilane, α-chloroethyltrichlorosilane, β-chloroethyltrichlorosilane, chloromethyldimethylchlorosilane, triorganosilylmercaptane, trimethylsilylmercaptane, triorganosilylacrylate, vinyldimethylacetoxysilane, dimethylethoxysilane, trimethylethoxysilane, trimethylmethoxysilane, methyltriethoxysilane, isobutyltrimethoxysilane, dimethyldimethoxysilane, diphenyldiethoxysilane, hexamethyldisiloxane, 1,3-divinyltetramethyldisiloxane, 1,3-diphenyltetramethyldisiloxane and dimethylpolysiloxane having 2 to 12 siloxane units per molecule and having 0 to 1 hydroxy group binding to Si at each unit positioned at an end. Additionally, silicone oil such as dimethylsilicone oil is mentioned. These may be used singly or a mixture of two or more types.

The flowability improver preferably has a number average particle diameter of 5 to 100 nm and further preferably 5 to 50 nm; and has a specific surface area (measured by nitrogen adsorption in accordance with the BET method) of preferably 30 $m^2/g$ or more, and more preferably 60 to 400 $m^2/g$. As a surface-treated fine-powder particle, 20 $m^2/g$ or more is preferable and 40 to 300 $m^2/g$ is particularly preferably. Preferable dose of these fine-powder particles is preferably 0.03 to 8 parts by mass relative to 100 parts by mass of a toner particle.

To the toner of the embodiment, other additives may be added. For example, for the purpose of protecting a photoreceptor and a carrier, improving cleaning performance, controlling heat property, electric property and physical property, controlling resistance and a softening point and improving a fixation rate, various types of metal soaps, fluorine surfactants, dioctyl phthalate; tin oxide, zinc oxide, carbon black and antimony oxide, as a conductivity imparting agent; and an inorganic fine powder particle formed of e.g., titanium oxide, aluminum oxide and alumina may be added, if necessary. Furthermore, these inorganic fine powder particles may be hydrophobized, if necessary. Furthermore, a lubricant such as polytetrafluoroethylene, zinc stearate and polyvinylidene fluoride; a polishing agent such as cesium oxide, silicon carbide and strontium titanate; a caking inhibitor; and further, a white fine particle and black fine particle having reverse polarity as that of a toner particle can be used in a small amount as a developing improver.

It is also preferable that these additives, for the purpose of controlling a charge amount, may be treated with a treatment agent including a silicone varnish, modified silicone varnishes in various ways, silicone oil, modified silicone oil in various ways, a silane coupling agent, a silane coupling agent having a functional group, other organic silicon compounds or other treatment agents.

In the embodiment, a charge control agent is sufficiently mixed and stirred with the aforementioned additives and a toner, by a mixer such as Henschel mixer, a ball mill, Nauta-mixer, a V-type mixer, a W-type mixer and a super mixer such that the additive is externally uniformly attached to the surface of a toner particle. In this manner, a desired toner for electrostatic charge development can be obtained.

The toner of the embodiment is thermally stable and can maintain stable charging characteristics without receiving thermal change during an electrophotographic process. Furthermore, since the toner is homogeneously dispersed in any binder resin, a fresh toner has very uniform charge distribution. Because of this, even in untransferred and recovered toner (waste toner) of the embodiment, saturated triboelectric charge amount and charge distribution rarely change compared to those of the fresh toner. However, when waste toner derived from the toner of the embodiment for electrostatic charge image development is reused, if a toner is produced by selecting a polyester resin containing an aliphatic diol as a binder resin or a styrene-acrylate copolymer crosslinked with a metal as a binder resin and adding a large amount of polyolefin to this, the difference between fresh toner and waste toner can be further reduced.

The toner of the embodiment can be produced by a known method. As a production method, for example, the aforementioned toner components, i.e., a binder resin, a charge control agent and a colorant, are sufficiently mixed by a mixer such as a ball mill. The mixture is sufficiently kneaded by a heated kneader such as a heated-roll kneader, cooled to solidify, ground and classified to obtain a toner. Such a grinding method is preferable.

The mixture may be dissolved in a solvent and sprayed to obtain fine particles followed by drying and classifying. In this manner, toner can be produced. Furthermore, toner can be produced by mixing predetermined materials with a monomer for constituting a binder resin to obtain emulsion or suspension solution, which is subjected to polymerization (called a polymerization method). In the case of a so-called microcapsule toner consisting of a core material and a shell material, predetermined materials are added to the core material or the shell material, or both of them to produce the toner. Moreover, the toner of the embodiment can be produced by sufficiently mixing desired additives as needed bases and a toner particle by a mixer such as Henschel mixer.

The method for producing the toner of the embodiment by the grinding method will be more specifically described below. First, a binder resin, a colorant, a charge control agent and other requisite additives are homogeneously mixed. For mixing, a known stirrer, for example, Henschel mixer, a super mixer and a ball mill may be used. The obtained mixture is subjected to hot-melt kneading using an airtight kneader, or a single-screw or a twin-screw extruder. The kneaded product is cooled and then roughly ground by use of a crusher or a hammer mill, and further finely ground by use of a grinder such as a jet mill or a high-speed rotatory mill. Furthermore, using an air classifier, such as an elbow jet of an inertial classification system using the Coanda effect, a microplex of the cyclone (centrifugation) classification system and a DS separator, classification is performed to obtain a predetermined particle size. Furthermore, if an external additive is applied to the surface of a toner, the toner and the external additive are mixed and stirred by a high speed stirrer such as Henschel mixer and a super mixer.

Furthermore, the toner of the embodiment can be produced also by a suspension polymerization method or an emulsion polymerization method. In the suspension polymerization, a polymerizable monomer, a colorant, a polymerization initiator, a charge control agent and, if necessary, other additives such as a crosslinking agent and a dispersion stabilizer are homogeneously dissolved or dispersed to prepare a monomer composition. Thereafter, the monomer composition is dispersed in a continuous phase, such as a water phase, containing a dispersion stabilizer by an appropriate stirrer or a disperser such as a homo-mixer, a homogenizer, an atomizer, a micro-fluidizer, a single-liquid fluid nozzle, a gas-liquid fluid nozzle and an electric emulsifier. Granulation is performed preferably by controlling the stirring rate, temperature and time such that liquid drops of the polymerizable monomer composition become equal to a desired toner particle size. Simultaneously, a polymerization reaction is performed at 40 to 90° C. to obtain toner particles having a desired particle size. The obtained toner particles are washed, filtrated and then dried. After toner particles are produced, an external additive may be added in accordance with the aforementioned treatment method.

The particles produced by the emulsion polymerization method are excellent in uniformity compared to the particles obtained by the aforementioned suspension polymerization method; however, an average particles size thereof is as extremely small as 0.1 to 1.0 µm. Therefore, as the case may be, the emulsified particles may be subjected to a so-called seed polymerization, in which the particles are grown by adding a polymerizable polymer with the emulsified particles used as nuclei. Alternatively, the emulsified particles can be adhered with each other or fused until an appropriate average particle size is obtained.

Production in accordance with these polymerization methods does not employ a grinding step. Therefore, toner particles do not become fragile. In addition, a substance having a low softening point, which is not easily used in conventional grinding methods, can be used in a large amount. Because of this, raw materials can be selected from a wide range. Since a hydrophobic material such as a mold-releasing agent and a colorant are rarely exposed on the surface of a toner particle, a toner holding member, a photoreceptor, a transfer roller and a fixing device are less contaminated.

By producing the toner of the embodiment in accordance with the polymerization method, properties such as image reproducibility, transfer property and color reproducibility can be further improved. To meet the requirement for fine dots, a toner having a small particle size and a narrow particle size distribution can be relatively easily obtained.

As the polymerizable monomer used for producing the toner of the embodiment by a polymerization method, a vinyl polymerizable monomer applicable to radical polymerization is used. As the vinyl polymerizable monomer, a mono-functional polymerizable monomer or a poly-functional polymerizable monomer can be used.

Examples of the mono-functional polymerizable monomer include styrene polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butyl styrene, p-n-hexylstyrene and p-phenylstyrene; acrylate polymerizable monomers such as methyl acrylate, ethyl acrylate, n-propyl acrylate, isopropyl acrylate, n-butyl acrylate, isobutyl acrylate, tert-butyl acrylate, n-amyl acrylate, n-hexyl acrylate, 2-ethylhexyl acrylate, n-octylacrylate, benzyl acrylate, dimethylphosphatemethyl acrylate, dibutylphosphateethyl acrylate and 2-benzoyloxyethyl acrylate; methacrylate polymerizable monomers such as methyl methacrylate, ethyl methacrylate, n-propyl methacrylate, isopropyl methacrylate, n-butyl methacrylate, isobutyl methacrylate, tert-butyl methacrylate, n-amyl methacrylate, n-hexyl methacrylate, 2-ethylhexyl methacrylate, n-octyl methacrylate, diethylphosphate methacrylate and dibutylphosphateethyl methacrylate; unsaturated aliphatic monocarboxylate; vinyl esters such as vinyl acetate, vinyl propionate and vinyl benzoate; vinyl ethers such as vinyl methyl ether and vinyl isobutyl ether; vinyl ketones such as vinyl methyl ketone, vinyl hexyl ketone and vinyl isopropyl ketone.

As the polymerization initiator to be used in producing the toner of the embodiment by a polymerization method, a known polymerization initiator such as an organic peroxide can be used. Examples of the water soluble polymerization initiator include ammonium persulfate, potassium persulfate, 2,2'-azobis(N,N'-dimethyleneisobutyroamidine) hydrochloride, 2,2'-azobis(2-aminodipropane) hydrochloride, azobis (isobutylamidine) hydrochloride, sodium 2,2'-azobisisobutyronitrilesulfonate, ferrous sulfate or hydrogen peroxide.

A polymerization initiator is preferably used in an amount of 0.5 to 20 parts by mass relative to 100 parts by mass of the polymerizable monomer. The polymerization initiators may be used singly or in combination. Examples of the dispersant used in producing a polymerized toner include inorganic oxides such as tricalcium phosphate, magnesium phosphate, aluminum phosphate, zinc phosphate, calcium carbonate, magnesium carbonate, aluminum hydroxide, calcium metasilicate, calcium sulfate, barium sulfate, bentonite, silica and alumina; and organic compounds such as polyvinyl alcohol, gelatin, methylcellulose, methylhydroxypropylcellulose, ethylcellulose, a sodium salt of carboxymethylcellulose and starch. These dispersants are preferably used in an amount of 0.2 to 2.0 parts by mass relative to 100 parts by mass of a polymerizable monomer.

As to these dispersants, commercially available products may be directly used. However, to obtain dispersion particles having fine and uniform particle size, the inorganic compound can be produced in a dispersive medium while stirring at a high speed.

When the toner obtained by the polymerization method is compared to the toner obtained by a grinding method without a specific treatment, degree of unevenness of a toner particle tends to be small. In addition, since the toner has indeterminate form, the area of an electrostatic latent image carrier in contact with a toner particle increases, adhesion force to a toner particle increases. As a result, contamination within a machine reduces and an image having further higher density and higher quality tends to be obtained.

Furthermore, even in the case of the toner obtained by the grinding method, the degree of unevenness in the surface of a toner particle can be reduced by a method such as a warm bath method in which toner particles are dispersed in water and heated, a heat treatment method in which toner particles are passed through hot air flow or a mechanical impact method in which mechanical energy is applied to treat toner particles. Examples of a useful apparatus for reducing the degree of unevenness include a mechanofusion system (manufactured by Hosokawa Micron Group) using a dry-process mechanochemical method, I-system jet mill, a hybridizer (manufactured by Nara Machinery Co., Ltd.) which is a mixing apparatus having a rotor and a liner, and a Henschel mixer, which is a mixer having high speed stirring vane.

The degree of unevenness of the toner particle can be expressed by an average degree of circularity value. The average degree of circularity (C) refers to a value obtained in the following manner. Degree of circularity (Ci) is obtained in accordance with the following formula (2) and further the sum of degree of circularity values of all particles measured is divided by the total number (m) of particles measured, in accordance with the following formula (3).

[Mathematical formula 1]

$$\text{Degree of circularity } (Ci) = \frac{\text{Boundary length of circle having the same projected area as that of particle}}{\text{Boundary length of projection image of particle}} \quad (2)$$

[Mathematical formula 2]

$$\text{Average degree of circularity } C = \sum_{i=1}^{m} Ci/m \quad (3)$$

The degree of circularity (Ci) is measured by a flow-system particle image analyzer (for example, FPIA-1000 manufactured by TOA Corporation). In a measurement method, a dispersion solution is prepared by dispersing a toner (about 5 mg) in water (10 ml) dissolving a nonion surfactant (about 0.1 mg) and ultrasonic wave (20 kHz, 50 W) is applied to the dispersion solution for 5 minutes to set a dispersion solution concentration to be 5,000 to 20,000 particles/μL, and then a degree of circularity distribution of particles having an equivalent circle diameter of 0.60 μm or more and less than 159.21 μm is measured by the flow system particle image measurement apparatus.

The average degree of circularity value is preferably 0.955 to 0.995 and further preferably 0.960 to 0.985. If the toner particles are prepared in this way, the phenomenon where remaining toner untransferred increases is reduced and retransfer tends not to occur.

In the case of the toner of the embodiment, in view of imaging performance and toner productivity, a volume average particle size of a toner, in the case of a grinded toner, measured by a laser grain size distribution measurement apparatus such as a microsizer (e.g., manufactured by Seishin Enterprise Co., Ltd.) preferably falls within the range of 2 to 15 μm and more preferably within the range of 3 to 12 μm. If the average particle size is beyond 15 μm, resolution or sharpness tend to decrease. In contrast, if the average particle size is less than 2 μm, resolution improves; however, yield decreases during a toner production process. As a result, problems of high cost and scattering of a toner within a machine occur and health problems such as skin penetration tend to occur.

On the other hand, in the case of a polymerized toner, the volume average particle size thereof preferably falls within the range of 3 to 9 μm, more preferably 4 to 8.5 μm and particularly preferably, 5 to 8 μm. If the volume average particle size is smaller than 4 μm, toner flowability decreases. As a result, charging performance of each particle tend to reduce. In addition, since charge distribution is widened, e.g., background fogging or leakage of a toner from a developing apparatus tend to occur. Furthermore, if the volume average particle size is smaller than 4 μm, it may be significantly hard to clean a machine. If the volume average particle size is larger than 9 μm, resolution reduces. As a result, sufficiently satisfactory quality of an image cannot be obtained and it may be difficult to satisfy high image quality demanded in recent years.

Furthermore, the polymerized toner of the embodiment has a volume average grain-size distribution index (GSDv) of preferably 1.15 to 1.30 and more preferably 1.15 to 1.25, the volume average grain-size distribution index being calculated from $(D84\%/D16\%)^{1/2}$, where the grain size distribution measured by the method described below is divided into grain-size ranges (channels) and cumulative distribution curves are prepared based on the volumes and numbers in ascending order from a smaller particle size, and the particle size corresponding to a cumulative volume of 16% is defined as volume D16%; the particle size corresponding to a cumulative volume of 50% is defined as volume D50%; and the particle size corresponding to a cumulative volume of 84% is defined as D84%.

As to the grain size distribution of a toner, in the case of the toner of the embodiment, when a grain size is measured, for example, by Coulter counter (TA-II manufactured by Coulter), the content of particles of 2 μm or less is desirably 10 to 90% on a number base and the content of particles of 12.7 μm or more is desirably 0 to 30% on a volume base.

Furthermore, it is desirable that uniformity of particle sizes (volume average particle size/number average particle diameter) is as high as 1.00 to 1.30.

In the case of a toner for electrostatic charge development of the embodiment, the specific surface area of a toner, which is measured by BET specific surface area using nitrogen as an adsorption and desorption gas, is preferably 1.2 to 5.0 m$^2$/g and more preferably 1.5 to 3.0 m$^2$/g. The specific surface area is measured, for example, by a BET specific surface area measurement apparatus (for example, FlowSorb II2300 manufactured by Shimadzu Corporation) and defined as a value obtained by removing a gas adsorbed onto the toner surface at 50° C. for 30 minutes, and then cooling with liquid nitrogen to allow nitrogen gas to be resorbed to the toner, and increasing the temperature again to 50° C. and obtaining the amount of desorption gas.

In the case of the toner of the embodiment, an apparent specific gravity (bulk density) was measured, for example, by a powder tester (for example, manufactured by Hosokawa Micron Group). In the case of a non-magnetic toner, the apparent specific gravity is preferably 0.2 to 0.6 g/cm$^3$. In the case of a magnetic toner, the apparent specific gravity thereof, which varies depending upon the type and content of the magnetic toner, is preferably 0.2 to 2.0 g/cm$^3$.

In the case of the toner of the embodiment, non-magnetic toner preferably has a true specific gravity of 0.9 to 1.2 g/cm$^3$. In the case of a magnetic toner, the true specific gravity thereof, which varies depending upon the type and content of a magnetic toner, is desirably 0.9 to 4.0 g/cm$^3$. The true specific gravity of a toner is calculated as follows. A toner (1.000 g) is weighed, put in a tableting machine of 10 mmϕ and compressed and molded while applying a pressure of 200 kgf/cm$^2$ under vacuum. The height of the resultant cylindrical product is measured by a micro meter. Based on this, a true specific gravity is calculated.

Flowability of a toner is defined by repose angles in the flow condition and the static condition, which are measured, for example, by a repose angle measurement apparatus (for example, manufactured by Tsutsui Scientific Instruments Co., Ltd.). The repose angle in the flow condition, in the case of the toner for electrostatic charge development containing the charge control agent of the embodiment, is desirably 5 to 45 degrees; whereas, the repose angle in the static condition is desirably 10 to 50 degrees.

The toner of the embodiment, more specifically, a grounded toner, preferably has an average value of shape factor (SF-1) within the range of 100 to 400 and an average value of shape factor 2 (SF-2) within the range of 100 to 350.

In the embodiment, shape factors of a toner, i.e., SF-1, SF-2, were obtained by magnifying toner particles 1000× by use of an optical microscope (for example, BH-2 manufactured by Olympus Corporation) equipped with, for example, a CCD camera, placing about 30 particle samples in a field of vision, taking an image, transferring it to an image analysis apparatus (for example, Luzex FS manufactured by Nireco Corporation) and repeating this process until about 1000 toner particles are counted to calculate shape factors. The shape factor (SF-1) and the shape factor 2 (SF-2) are calculated in accordance with the following formulae.

$$SF\text{-}1 = ((ML^2 \times \pi)/4A) \times 100$$

(in the formula, ML represents the maximum length of a particle and A represents the projected area of a single particle)

$$SF\text{-}2 = (PM^2/4A\pi) \times 100$$

(in the formula, PM represents the boundary length of a particle and A represents the projected area of a single particle).

SF-1 represents distortion of a particle. As the particle becomes closer to a sphere, SF-1 becomes closer to 100. As a particle becomes long and thin, the numerical value increases. In contrast, SF-2 represents unevenness of a particle. As the particle becomes closer to a sphere, SF-2 becomes closer to 100. As a particle becomes complicated, the numerical value increases.

The toner of the embodiment, more specifically, a non-magnetic toner, desirably has a volume resistivity of $1\times10^{12}$ to $1\times10^{16}$ Ωcm. In contrast, in the case of a magnetic toner, the volume resistivity thereof, which varies depending upon the type and content of magnetic toner, is desirably $1\times10^{8}$ to $1\times10^{16}$ Ωcm. The toner volume resistivity in this case is defined as a value obtained by compressing and molding a toner particle to prepare a disk-form test piece having a diameter of 50 mm and a thickness of 2 mm, setting the test piece on an electrode (for example, SE-70 manufactured by Ando Electric Co., Ltd.) for a solid substance, continuously applying a direct current voltage of 100 V for one hour and measuring by a highly insulating resistance meter (for example, 4339A manufactured by Hewlett-Packard Company).

The toner of the embodiment, more specifically, a non-magnetic toner desirably has a dielectric loss tangent of $1.0\times10^{-3}$ to $15.0\times10^{-3}$. In the case of a magnetic toner, the dielectric loss tangent thereof, which varies depending upon the type and content of magnetic toner, is desirably $2\times10^{-3}$ to $30\times10^{-3}$. In this case, the dielectric loss tangent of a toner is defined as a value (Tan δ) obtained by compressing and molding a toner particle to prepare a disk-form test piece having a diameter of 50 mm and a thickness of 2 mm, setting the test piece on an electrode for a solid substance, and measuring by an LCR meter (for example, 4284A manufactured by Hewlett-Packard Company) at a measurement frequency of 1 KHz, a peak-to-peak voltage of 0.1 KV.

The toner of the embodiment desirably has an Izod impact value of 0.1 to 30 kg cm/cm. In this case, the Izod impact value of the toner is obtained by preparing a plate-form test piece by thermofusion of a toner particle and measuring the test piece in accordance with JIS standard K-7110 (impact strength analysis of hard plastic).

The toner of the embodiment desirably has a melt index (MI value) of 10 to 150 g/10 min. In this case, the melt index (MI value) is obtained by measurement in accordance with JIS standard K-7210 (A method). In this case, the measurement temperature is 125° C. and weight is set to 10 kg.

The toner of the embodiment desirably has a melting onset temperature of 80 to 180° C. and a 4 mm-down temperature of 90 to 220° C. In this case, the melting onset temperature of the toner is obtained by compressing and molding a toner particle to prepare a disk-form test piece having a diameter of 10 mm and a thickness of 20 mm, setting this in a thermal fusion property measurement apparatus, for example, a flow tester (for example, CFT-500C manufactured by Shimadzu Corporation) and measuring by applying a load of 20 kgf cm$^2$; and defined as a (temperature) value at which melting starts and a piston starts moving down. Furthermore, in the same measurement, the temperature at which the piston moves down by 4 mm is defined as the 4 mm-down temperature.

The toner of the embodiment desirably has a glass transition temperature (Tg) of 35 to 80° C. and more desirably 40 to 75° C. In this case, the glass transition temperature of a toner is measured by use of a differential thermal analysis (hereinafter, simply referred to as DSC) apparatus by increasing temperature at a predetermined rate, rapidly cooling and again increasing the temperature to cause a phase change. The glass transition temperature is defined as a value obtained from a peak value of the phase change. If the Tg of a toner is below 35° C., offset resistance and storage stability tend to reduce. In contrast, when the Tg is beyond 80° C., fixation strength of an image tends to decrease.

In DSC measurement of the toner of the embodiment, as to the endothermic peak observed, the peak top temperature of a maximum peak is preferably present within the range of 70 to 120° C.

The toner of the embodiment desirably has a melt viscosity of 1,000 to 50,000 poises and more preferably 1,500 to 38,000 poises. In this case, the toner melt viscosity is defined as a value obtained by compressing and molding a toner particle to prepare a disk-form test piece having a diameter of 10 mm and a thickness of 20 mm and setting this in a thermal fusion property measurement apparatus, for example, a flow tester (for example, CFT-500C manufactured by Shimadzu Corporation) and measuring by applying a load of 20 kgf/cm$^2$.

The toner of the embodiment contains insoluble matter in solvent preferably in an amount of 0 to 30 mass % in terms of THF insoluble matter, 0 to 40 mass % in terms as ethyl acetate insoluble matter and 0 to 30 mass % in terms of chloroform insoluble matter. The content of insoluble matter in solvent is defined a value obtained by homogeneously dissolving or dispersing a toner (1 g) in THF, ethyl acetate and chloroform (each solvent: 100 ml), filtrating the resultant solution or dispersion solution through a pressure filter, drying the resultant filtrate, quantifying the filtrate and calculating the ratio of the insoluble matter in an organic solvent relative to the toner.

The toner of the embodiment can be used in one of the image forming methods, i.e., a single-component development system. The single-component development system refers to a system of developing a latent image by supplying a toner of thin-film form to a latent image carrier. A toner is formed into a thin film by using an apparatus generally having a toner transfer member, a toner-layer thickness regulation member and a toner supply auxiliary member, in which the toner supply auxiliary member is in contact with the toner transfer member and the toner-layer thickness regulation member is in contact with the toner transfer member.

The case where the toner of the embodiment is applied to a two-component developing method will be more specifically described. The two-component development system refers to a system using a toner and a carrier (serving as a charge imparting material and a toner transport material). As the carrier, the aforementioned magnetic material or glass beads are used. The developer (toner and carrier) is stirred by a stirring member to generate a predetermined amount of charge and transferred by a magnet roller to a developing site. On the magnet roller, the developer is held on the roller surface by magnetic force to form a magnetic brush in the form of a layer regulated to have an appropriate height by a developer regulating board, etc. The developer migrates on the roller in accordance with a rotation of the developing roller and comes into contact with an electrostatic latent image holder or to face the holder in non-contact with each other with regular interval interposed between them to develop and visualize the latent image. When development is performed in a non-contact state, a toner can acquire driving force capable of flying over a space of a predetermined interval generally by generating a direct-current electric field between the developer and the latent image holder. To develop into a further clearer image, the toner can be applied to a system of superimposing alternating current.

Furthermore, the charge control agent to be used in the embodiment is further suitable as a charge control agent (charge augmenting agent) in an electrostatic powder coating paint. More specifically, the electrostatic coating paint using the charge augmenting agent is excellent in environment resistance, storage stability, particularly, heat stability and durability, and can form a thick film having a coating efficiency of 100% without coating defects.

EXAMPLES

The present invention will be described in more detail based on Examples below, which should not be construed as limiting the present invention. In Examples below, "parts" all represent "parts by mass".

The thiazolidinedione derivative represented by formula (1) was purified by column chromatography, adsorption by means of silica gel, active carbon or activated soil, recrystallization using a solvent, crystallization or the like.

A compound was identified by NMR analysis.

Synthesis Example 1

Synthesis of Exemplary Compound No. 2

To a reaction container purged with nitrogen, 4-methylbenzaldehyde (12.0 g), thiazolidine-2,4-dione (11.7 g), piperidine (0.9 g) and ethanol (100 ml) were added and heated to reflux for 7 hours while stirring. The reaction solution was cooled to room temperature and a precipitated crystal was collected by filtration and then soaked and washed with ethanol to obtain 5-(4-methyl)benzylidene-thiazolidine-2,4-dione (exemplary compound No. 2) as a pale yellow crystal (17.8 g (yield 81%)).

The structure of the obtained pale yellow crystal was identified by using NMR.

The following 8 signals of hydrogen were detected by $^1$H-NMR (DMSO-$d_6$). δ (ppm)=7.76 (1H), 7.50-7.48 (2H), 7.35-7.34 (2H), 2.36 (3H).

Synthesis Example 2

Synthesis of Exemplary Compound No. 3

To a reaction container purged with nitrogen, 2-methylbenzaldehyde (8.0 g), thiazolidine-2,4-dione (7.8 g), piperidine (0.6 g) and ethanol (100 ml) were added and heated to reflux for 13 hours while stirring. The reaction solution was cooled to room temperature and a precipitated crystal was collected by filtration and then soaked and washed with ethanol to obtain 5-(2-methyl)benzylidene-thiazolidine-2,4-dione (exemplary compound No. 3) as a pale yellow crystal (10.4 g (yield 71%)).

The structure of the obtained pale yellow crystal was identified by using NMR. Measurement results of 1H-NMR are shown in FIG. 1.

The following 8 signals of hydrogen were detected by $^1$H-NMR (DMSO-$d_6$). δ (ppm)=7.89 (1H), 7.43-7.33 (4H), 2.39 (3H).

Synthesis Example 3

Synthesis of Exemplary Compound No. 4

To a reaction container purged with nitrogen, 3-methylbenzaldehyde (8.0 g), thiazolidine-2,4-dione (7.8 g), piperidine (0.6 g) and ethanol (100 ml) were added and heated to reflux for 13 hours while stirring. The reaction solution was cooled to room temperature and a precipitated crystal was collected by filtration and then soaked and washed with ethanol to obtain 5-(3-methyl)benzylidene-thiazolidine-2,4-dione (exemplary compound No. 4) as a pale yellow crystal (9.3 g (yield 64%)).

The structure of the obtained pale yellow crystal was identified by using NMR.

The following 8 signals of hydrogen were detected by $^1$H-NMR (DMSO-$d_6$). δ (ppm)=7.73 (1H), 7.43-7.37 (3H), 7.34-7.28 (1H), 2.36 (3H).

Synthesis Example 4

Synthesis of Exemplary Compound No. 5

To a reaction container purged with nitrogen, benzaldehyde (6.5 g), thiazolidine-2,4-dione (7.0 g), anhydrous sodium acetate (14.8 g) and acetic acid (100 ml) were added and heated to reflux for 72 hours while stirring. The reaction solution was cooled to room temperature, added to water (500 ml) and stirred for 30 minutes. A precipitated crystal was collected by filtration and then soaked and washed with water to obtain 5-benzylidene-thiazolidine-2,4-dione (exemplary compound No. 5) as a pale yellow crystal (9.9 g (yield 81%)).

The structure of the obtained pale yellow crystal was identified by using NMR.

The following 6 signals of hydrogen were detected by $^1$H-NMR (DMSO-$d_6$). δ (ppm)=7.80 (1H), 7.62-7.59 (2H), 7.56-7.52 (2H), 7.51-7.47 (1H).

Synthesis Example 5

Synthesis of Exemplary Compound No. 6

To a reaction container purged with nitrogen, 4-tert-butylbenzaldehyde (16.2 g), thiazolidine-2,4-dione (11.7 g), piperidine (0.9 g) and ethanol (100 mL) were added and heated to reflux for 8 hours while stirring. The reaction solution was cooled to room temperature and a precipitated crystal was collected by filtration and then soaked and washed with ethanol to obtain 5-(4-tert-butyl)benzylidene-thiazolidine-2,4-dione (exemplary compound No. 6) as a pale yellow crystal (13.3 g (yield 51%)).

Figure 2:
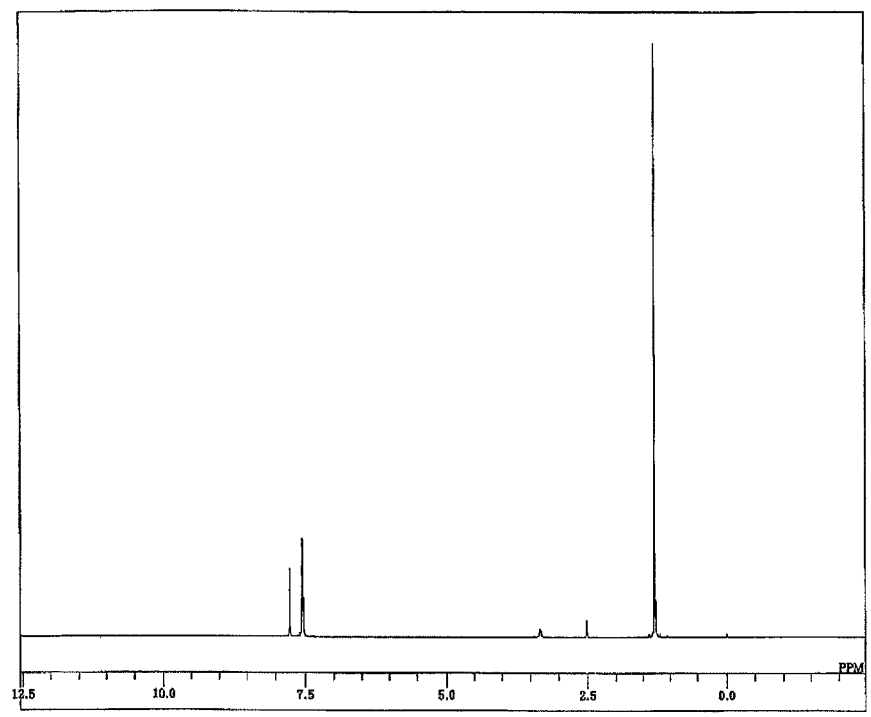
FIG. 2 is a $^1$H-NMR chart of a compound (Exemplary Compound No. 6) of Synthesis Example 5.

The structure of the obtained pale yellow crystal was identified by using NMR. Measurement results of 1H-NMR are shown in FIG. 2.

The following 14 signals of hydrogen were detected by $^1$H-NMR (DMSO-$d_6$). δ (ppm)=7.77 (1H), 7.60-7.50 (4H), 1.30 (9H).

Synthesis Example 6

Synthesis of Exemplary Compound No. 7

To a reaction container purged with nitrogen, 4-methoxybenzaldehyde (10.2 g), thiazolidine-2,4-dione (8.8 g), anhydrous sodium acetate (18.7 g) and acetic acid (150 ml) were added and heated to reflux for 24 hours while stirring. The reaction solution was cooled to room temperature, added to water (500 ml) and stirred for 30 minutes. A precipitated crystal was collected by filtration and then soaked and washed with water to obtain 5-(4-methoxy)benzylidene-thiazolidine-2,4-dione (exemplary compound No. 7) as a pale yellow crystal (7.4 g (yield 42%)).

The structure of the obtained pale yellow crystal was identified by using NMR.

The following 8 signals of hydrogen were detected by $^1$H-NMR (DMSO-$d_6$). δ (ppm)=7.75 (1H), 7.57-7.55 (2H), 7.11-7.09 (2H), 3.83 (3H).

Synthesis Example 7

Synthesis of Exemplary Compound No. 8

To a reaction container purged with nitrogen, 3-methoxybenzaldehyde (13.6 g), thiazolidine-2,4-dione (11.7 g), anhydrous sodium acetate (24.9 g) and acetic acid (120 ml) were added and heated to reflux for 48 hours while stirring. The reaction solution was cooled to room temperature, added to water (400 ml) and stirred for 30 minutes. A precipitated crystal was collected by filtration and then soaked and washed with water to obtain 5-(3-methoxy)benzylidene-thiazolidine-2,4-dione (exemplary compound No. 8) as a pale yellow crystal (18.9 g (yield 80%)).

The structure of the obtained pale yellow crystal was identified by using NMR.

The following 8 signals of hydrogen were detected by $^1$H-NMR (DMSO-$d_6$). δ (ppm)=7.77 (1H), 7.46-7.44 (1H), 7.17-7.14 (2H), 7.07-7.04 (1H), 3.84 (3H).

Synthesis Example 8

Synthesis of Exemplary Compound No. 9

To a reaction container purged with nitrogen, 2-methoxybenzaldehyde (13.6 g), thiazolidine-2,4-dione (11.7 g), anhydrous sodium acetate (24.9 g) and acetic acid (200 ml) were added and heated to reflux for 50 hours while stirring. The reaction solution was cooled to room temperature, added to water (400 ml) and stirred for 30 minutes. A precipitated crystal was collected by filtration and then soaked and washed with water to obtain 5-(2-methoxy)benzylidene-thiazolidine-2,4-dione (exemplary compound No. 9) as a pale yellow crystal (19.3 g (yield 82%)).

The structure of the obtained pale yellow crystal was identified by using NMR.

The following 8 signals of hydrogen were detected by $^1$H-NMR (DMSO-$d_6$). δ (ppm)=7.96 (1H), 7.47-7.45 (1H), 7.41-7.38 (1H), 7.15-7.12 (1H), 7.09-7.07 (1H), 3.87 (3H).

Synthesis Example 9

Synthesis of Exemplary Compound No. 29

To a reaction container purged with nitrogen, 3-chlorobenzaldehyde (8.00 g), thiazolidine-2,4-dione (6.66 g), piperidine (0.5 g) and ethanol (100 ml) were added and heated to reflux for 8.5 hours while stirring. The reaction solution was cooled to room temperature and a precipitated crystal was collected by filtration and then soaked and washed with ethanol to obtain 5-(3-chloro)benzylidene-thiazolidine-2,4-dione (exemplary compound No. 29) as a pale yellow crystal (8.73 g (yield 64.2%)).

The structure of the obtained pale yellow crystal was identified by using NMR.

The following 5 signals of hydrogen were detected by $^1$H-NMR (DMSO-$d_6$). δ (ppm)=7.78 (1H), 7.67 (1H), 7.52-7.58 (3H).

Synthesis Example 10

Synthesis of Exemplary Compound No. 30

To a reaction container purged with nitrogen, 2,5-dimethoxybenzaldehyde (16.61 g), thiazolidine-2,4-dione (11.73 g), anhydrous sodium acetate (24.91 g) and acetic acid (75 ml) were added and heated to reflux for 24 hours while stirring. The reaction solution was cooled to room temperature, added to water (600 ml) and stirred for 30 minutes. A precipitated crystal was collected by filtration and then soaked and washed with water to obtain 5-(2,5-dimethoxy)benzylidene-thiazolidine-2,4-dione (exemplary compound No. 30) as a pale orange crystal (25.0 g (yield 94.1%)).

The structure of the obtained pale orange crystal was identified by using NMR.

The following 10 signals of hydrogen were detected by $^1$H-NMR (DMSO-$d_6$). δ (ppm)=7.91 (1H), 7.08-7.10 (2H), 6.90-6.91 (1H), 3.84 (3H), 3.76 (3H).

Synthesis Example 11

Synthesis of Exemplary Compound No. 31

To a reaction container purged with nitrogen, acetophenone (24.03 g), thiazolidine-2,4-dione (23.43 g), anhydrous sodium acetate (49.82 g) and acetic acid (300 ml) were added and heated to reflux for a week while stirring. The reaction solution was cooled to room temperature, added to water (300 ml) and stirred for 30 minutes. A precipitated crystal was collected by filtration and then soaked and washed with n-butanol. Purification was performed by recrystallization using methanol to obtain 5-(α-methylbenzylidene)-thiazolidine-2,4-dione (exemplary compound No. 31) as a pale orange crystal (1.06 g (yield 2.42%)).

The structure of the obtained pale orange crystal was identified by using NMR.

The following 8 signals of hydrogen were detected by $^1$H-NMR (DMSO-$d_6$). δ (ppm)=7.39-7.46 (5H), 2.63 (3H).

Synthesis Example 12

Synthesis of Exemplary Compound No. 32

To a reaction container purged with nitrogen, piperonal (15.01 g), thiazolidine-2,4-dione (11.73 g), anhydrous sodium acetate (24.91 g) and acetic acid (75 ml) were added and heated to reflux for 24 hours while stirring. The reaction solution was cooled to room temperature, added to water (300 ml) and stirred for 30 minutes. A precipitated crystal was collected by filtration and then soaked and washed with water to obtain 5-(3,4-methylenedioxy)benzylidene-thiazolidine-2,4-dione (exemplary compound of No. 32) as a pale orange crystal (22.02 g (yield 88.3%)).

The structure of the obtained pale orange crystal was identified by using NMR.

The following 6 signals of hydrogen were detected by $^1$H-NMR (DMSO-$d_6$). δ (ppm)=7.72 (1H), 7.08-7.16 (3H), 6.13 (2H).

Example 13

Production of Non-Magnetic Toner 1

A styrene-acrylate copolymer resin (trade name CPR-100, acid value 0.1 mg KOH/g, manufactured by Mitsui Chemicals Inc.) (91 parts), the thiazolidinedione derivative (Exemplary Compound No. 3)(1-part) synthesized in Synthesis Example 2, carbon black (trade name MA-100 manufactured by Mitsubishi Chemical Corporation)(5 parts) and a low molecular weight polypropylene (trade name Viscol 550P, manufactured by Sanyo Chemical Industries, Ltd.)(3 parts) were melt-blended at 130° C. in a heat mixing apparatus (twin screw extrusion-kneading machine). The mixture was cooled and roughly ground by a hammer mill and then finely ground by a jet mill, and classified to obtain a non-magnetic toner having a volume average particle size of 9±0.5 μm.

(Evaluation of Non-Magnetic Toner 1)

The toner obtained was mixed with a non-coated ferrite carrier (F-150, manufactured by Powdertech) in a ratio of 4:100 parts by mass (a toner: carrier) and shaken to charge the toner negatively. Thereafter, the amount of charge was measured by a blow-off powder charge amount measurement apparatus. The results are collectively shown in Table 1.

Furthermore, time constant (τ), which is an index of a charge rising property was calculated. The time constant (τ) was obtained by measuring a charge amount at predetermined time intervals by a blow-off powder charge amount measurement apparatus (see, for example, Non Patent Literature 1) until saturated charge amount, and calculating $\ln(q^{max}-q)$ in accordance with the following formula, plotting time t and $\ln(q^{max}-q)$ to obtain a graph showing the relationship between the two factors. The results are collectively shown in Table 1.

$$(q^{max}-q)/(q^{max}-q^0)=\exp(-t/\tau)$$

where $q^{max}$ represents a saturated charge amount; $q^0$ represents an initial charge amount (in this case, charging time was 10 seconds), t represents each measurement time, the charge amount at that time is represented by q.

As the charge rising property becomes excellent, the value of time constant decreases. Time constant is measured in units of seconds.

Similarly, also in the case of mixing with a silicon coated ferrite carrier (F96-150, manufactured by Powdertech), charge amount and time constant were evaluated. The results are collectively shown in Table 1.

Example 14

Production and Evaluation of Non-Magnetic Toner 2

Non-magnetic toner 2 was prepared in the same manner as in Example 13 except that, in Example 13, the thiazolidinedione derivative (Exemplary Compound No. 3) synthesized in Synthesis Example 2 was replaced with the thiazolidinedione derivative (Exemplary Compound No. 6) synthesized in Synthesis Example 5, and the charge amount and time constant were evaluated by a blow-off powder charge amount measurement apparatus. The results are collectively shown in Table 1.

Example 15

Production and Evaluation of Non-Magnetic Toner 3

Non-magnetic toner 3 was prepared in the same manner as in Example 13 except that, in Example 13, the thiazolidinedione derivative (Exemplary Compound No. 3) synthesized in Synthesis Example 2 was replaced with the thiazolidinedione derivatives (Exemplary Compound No. 30) synthesized in Synthesis Example 10, and the charge amount and time constant were evaluated by a blow-off powder charge amount measurement apparatus. The results are collectively shown in Table 1.

Comparative Example 1

Production and Evaluation of Comparative Non-Magnetic Toner

For comparison, a comparative non-magnetic toner was prepared in the same manner as in Example 13 except that, in Example 13, the thiazolidinedione derivative (Exemplary Compound No. 3) synthesized in Synthesis Example 2 was replaced with a salt of 3,5-tert-butyl salicylic acid and zinc and the charge amount and time constant were evaluated by a blow-off powder charge amount measurement apparatus. The results are collectively shown in Table 1.

TABLE 1

| | Carrier F-150 | | Carrier F96-150 | |
|---|---|---|---|---|
| Toner | Charge amount (μc/g) | Time constant τ (s) | Charge amount (μc/g) | Time constant τ (s) |
| Example 13 | −39.8 | 105 | −27.7 | 103 |
| Example 14 | −25.2 | 121 | −27.3 | 101 |
| Example 15 | −40.1 | 106 | −28.0 | 102 |
| Comparative Example 1 | −23.0 | 200 | −15.0 | 108 |

As is apparent from Table 1, it was found that, in the toner using a charge control agent containing a thiazolidinedione derivative represented by formula (1) of the present invention as an active substance(s), charge rising property is improved and charge amount increases.

Example 16

Preparation of Resin Dispersion Solution

A polyester resin (DIACRON ER-561, manufactured by Mitsubishi Rayon Co., Ltd.)(80 parts), ethyl acetate (320 parts) and isopropyl alcohol (32 parts) were mixed. While stirring the mixture by a homogenizer (foam-less mixer, NGM-0.5TB, manufactured by Beryu Co. Ltd.) at 5,000 to 10,000 rpm, an appropriate amount of 0.1 mass % ammonia water was added dropwise to the mixture to perform phase inversion emulsification. Furthermore, the solvent was removed while reducing pressure by an evaporator to obtain a resin dispersion solution. The volume average particle size of the resin particle in the dispersion solution was 0.2 μm (the resin particle concentration was set to 20 mass % by adjusting it with ion exchange water).

(Preparation of Charge Control Agent Dispersion Solution)

Sodium dodecylbenzenesulfonate (0.2 parts), Sorbon T-20 (manufactured by TOHO Chemical Industry Co., Ltd.)(0.2 parts) and ion exchange water (17.6 parts) were mixed and dissolved. To this, the thiazolidinedione derivative (Exemplary Compound No. 3)(2.0 parts) synthesized in Synthesis Example 2 and zirconia beads (particle size of the beads: 0.65 mmφ, 15 ml equivalent) were added and dispersed with a paint conditioner (Red Devil No. 5400-5L manufactured by UNION N.J. (USA)) for 3 hours. The zirconia beads were removed by a sieve and adjusted with ion exchange water to obtain a 10 mass % charge control agent dispersion solution.

(Preparation of Polymerized Toner)

To a reaction container equipped with a thermometer, a pH meter and a stirrer, the resin dispersion solution (125 parts), an aqueous 20 mass % sodium dodecylbenzenesulfonate solution (1.0 part) and ion exchange water (125 parts) were added. The solution mixture was stirred at a rotation speed of 150 rpm for 30 minutes while controlling the temperature of the solution at 30° C. To this, an aqueous 1 mass % nitric acid solution was added and pH was adjusted to 3.0. The mixture was further stirred for 5 minutes. While the mixture was dispersed by a homogenizer (Ultra-TURRAX T-25 manufactured by IKA Japan), polyaluminum chloride (0.125 parts) was added to the mixture. After the liquid temperature was raised to 50° C., the mixture was further dispersed for 30 minutes. After the resin dispersion solution (62.5 parts) and the charge control agent dispersion solution (4.0 parts) were added, an aqueous 1 mass % nitric acid solution was added to adjust pH to 3.0, and dispersed further for 30 minutes. While stirring the mixture by a stirrer at 400 to 700 rpm, an aqueous 5 mass % sodium hydroxide solution (8.0 parts) was added. The mixture was continuously stirred until the volume average particle size of the toner reached 9.5 μm. After liquid temperature was raised to 75° C., the mixture was stirred further for 2 hours. After the volume average particle size was confirmed to reach 6.0 μm and spherical particles were obtained, the mixture was rapidly cooled with ice water. The particles were collected by filtration and subjected to dispersion washing with ion exchange water. Dispersion washing was repeated until the electric conductivity of the filtrate of the dispersion solution reached 20 μS/cm or less. Thereafter, the filtrate was dried by a dryer at 40° C. to obtain toner particles.

The toner particles thus obtained were classified by a sieve having 166 meshes (mesh size: 90 μm) to obtain a toner for evaluation.

(Evaluation)

The toner (2 parts) for evaluation thus obtained was mixed with a silicon coated ferrite carrier (F96-150 manufactured by Powdertech) (100 parts) and shaken to charge the toner negatively. Thereafter, the saturated charge amount was measured by a blow-off powder charge amount measurement apparatus under atmosphere of a temperature of 25° C. and a humidity of 50%. As a result, the saturated charge amount was −39.6 μC/g.

Example 17

A toner was prepared in the same conditions as in Example 16 by replacing the thiazolidinedione derivative (exemplary compound No. 3) synthesized in Synthesis Example 2 as is in Example 16 with the thiazolidinedione derivative (exemplary compound No. 30) synthesized in Synthesis Example 10, and the saturated charge amount of the toner was measured. As a result, the saturated charge amount was −40.2 μC/g.

Comparative Example 2

For comparison, a toner was prepared in the same conditions as in Example 16 except that the operation of adding a charge control agent dispersion solution in Example 16 was not performed and saturated charge amount was measured. As a result, the saturated charge amount was −20.5 μC/g.

As is apparent from the above results, a polymerized toner containing a thiazolidinedione derivative represented by formula (1) of the present invention as an active substance exhibits excellent charging performance.

More specifically, a polymerized toner having high charging performance can be obtained by use of a charge control agent containing a thiazolidinedione derivative represented by formula (1) of the present invention as an active substance.

INDUSTRIAL APPLICABILITY

A thiazolidinedione derivative represented by formula (1) of the present invention has excellent charging performance and a charge control agent containing the compound as an active substance has an apparently higher charging performance and more excellent environmental stability than those of conventional charge control agents. The charge control agent is suitable for a color toner, particularly for a polymerized toner. Furthermore, since a heavy metal such as a chromium compound, which is an environmental concern, is not contained, an extremely useful toner can be provided.

The invention claimed is:

1. A charge control agent containing, as an active substance(s), one or two or more thiazolidinedione derivatives represented by the following formula (1):

[Chemical Formula 1]

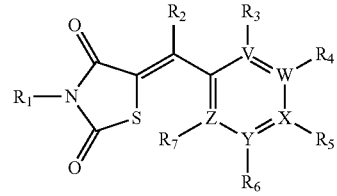

(1)

wherein $R_1$ represents a hydrogen atom, a linear or branched alkyl group having 1 to 8 carbon atoms which may have a substituent, a cycloalkyl group having 5 to 10 carbon atoms which may have a substituent, a substituted or unsubstituted aromatic hydrocarbon group, a substituted or unsubstituted heterocyclic group or a substituted or unsubstituted condensed polycyclic aromatic group; $R_2$ represents a hydrogen atom, a linear or branched alkyl group having 1 to 8 carbon atoms which may have a substituent, a cycloalkyl group having 5 to 10 carbon atoms which may have a substituent, a linear or branched alkenyl group having 2 to 6 carbon atoms which may have a substituent, a linear or branched alkyloxy group having 1 to 8 carbon atoms which may have a substituent, a cycloalkyloxy group having 5 to 10 carbon atoms which may have a substituent, a substituted or unsubstituted aromatic hydrocarbon group, a substituted or unsubstituted heterocyclic group, a substituted or unsubstituted condensed polycyclic aromatic group or a substituted or unsubstituted aryloxy group; $R_3$ to $R_7$, which may be identical to or different from each other, represent a hydrogen atom, a deuterium atom, a fluorine atom, a chlorine atom, a bromine atom, an iodine atom, a hydroxy group, a cyano group, a nitro group, a linear or branched alkyl group having 1 to 10 carbon atoms which may have a substituent, a cycloalkyl group having 5 to 10 carbon atoms which may have a substituent, a linear or branched alkenyl group having 2 to 6 carbon atoms which may have a substituent, a linear or branched alkyloxy group having 1 to 8 carbon atoms which may have a substituent, a cycloalkyloxy group having 5 to 10 carbon atoms which may have a substituent, a substituted or unsubstituted aromatic hydrocarbon group, a substituted or unsubstituted heterocyclic group, a substituted or unsubstituted condensed polycyclic aromatic group or a substituted or unsubstituted aryloxy group, and $R_3$ to $R_7$ may be joined to each other to form a ring; and V, W, X, Y and Z represent a carbon atom or a nitrogen atom and 0 to 3 of any of V, W, X, Y and Z are a nitrogen atom which does not have substituents of $R_3$ to $R_7$.

2. The charge control agent according to claim 1, wherein $R_1$ in the formula (1) is a hydrogen atom.

3. The charge control agent according to claim 1, wherein $R_2$ in the formula (1) is a hydrogen atom or a methyl group.

4. The charge control agent according to claim 1, wherein V, W, X, Y and Z in the formula (1) are all carbon atoms.

5. A charge control agent containing, as an active substance(s), one or two or more thiazolidinedione derivatives represented by the following formula (1'):

[Chemical Formula 2]

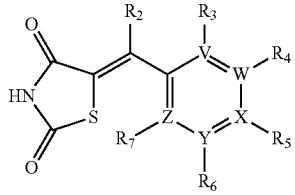

(1')

wherein $R_2$ represents a hydrogen atom, a linear or branched alkyl group having 1 to 8 carbon atoms which may have a substituent; and $R_3$ to $R_7$, which may be identical to or different from each other, represent a hydrogen atom, a deuterium atom, a chlorine atom, a cyano group, a nitro group, a linear or branched alkyl group having 1 to 10 carbon atoms which may have a substituent, a linear or branched alkenyl group having 2 to 6 carbon atoms which may have a substituent, a linear or branched alkyloxy group having 1 to 8 carbon atoms which may have a substituent, and $R_3$ to $R_7$ may be joined to each other to form a ring; and V, W, X, Y and Z represent a carbon atom or a nitrogen atom and 0 or 1 of any of V, W, X, Y and Z is a nitrogen atom which does not have substituents of $R_3$ to $R_7$.

6. A charge control agent containing, as an active substance(s), one or two or more thiazolidinedione derivatives represented by the following formula (1"):

[Chemical Formula 3]

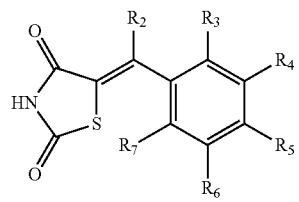

(1")

wherein $R_2$ represents a hydrogen atom, a linear or branched alkyl group having 1 to 6 carbon atoms which does not have a substituent; and $R_3$ to $R_7$, which may be identical to or different from each other, represent a hydrogen atom, a chlorine atom, a linear or branched alkyl group having 1 to 6 carbon atoms which does not have a substituent, a linear or branched alkenyl group having 2 to 4 carbon atoms which does not have a substituent, a linear or branched alkyloxy group having 1 to 6 carbon atoms which does not have a substituent, and $R_3$ to $R_7$ may be joined to each other to form a ring.

7. A toner containing the charge control agent according to claim 1, a colorant and a binder resin.

8. A polymerized toner containing the charge control agent according to claim 1, a colorant and a binder resin.

9. A toner containing the charge control agent according to claim 5, a colorant and a binder resin.

10. A toner containing the charge control agent according to claim 6, a colorant and a binder resin.

11. A polymerized toner containing the charge control agent according to claim 5, a colorant and a binder resin.

12. A polymerized toner containing the charge control agent according to claim 6, a colorant and a binder resin.

* * * * *